US008658670B2

(12) United States Patent
Guiles et al.

(10) Patent No.: US 8,658,670 B2
(45) Date of Patent: *Feb. 25, 2014

(54) METHODS AND COMPOUNDS FOR TREATMENT OF CLOSTRIDIUM BASED INFECTION

(75) Inventors: Joseph Guiles, Lafayette, CO (US); Xicheng Sun, Superior, CO (US); Nebojsa Janjic, Boulder, CO (US); Sarah Strong, Louisville, CO (US)

(73) Assignee: Crestone, Inc., Boulder, CO (US)

( * ) Notice: Subject to any disclaimer, the term of this patent is extended or adjusted under 35 U.S.C. 154(b) by 1465 days.

This patent is subject to a terminal disclaimer.

(21) Appl. No.: 11/853,636

(22) Filed: Sep. 11, 2007

(65) Prior Publication Data

US 2009/0163536 A1 Jun. 25, 2009

Related U.S. Application Data

(60) Provisional application No. 60/826,957, filed on Sep. 26, 2006.

(51) Int. Cl.
*A01N 43/42* (2006.01)
*A61K 31/44* (2006.01)
*A01N 43/90* (2006.01)
*A61K 31/47* (2006.01)
*C07D 491/02* (2006.01)
*C07D 498/02* (2006.01)
*C07D 513/02* (2006.01)
*C07D 515/02* (2006.01)

(52) U.S. Cl.
USPC ........... 514/301; 514/310; 514/312; 546/114; 546/153

(58) Field of Classification Search
USPC .......... 514/301, 395, 383, 438, 310; 546/114, 546/153
See application file for complete search history.

(56) References Cited

U.S. PATENT DOCUMENTS

| 4,710,506 | A | 12/1987 | Davies et al. |
| 6,943,175 | B2 | 9/2005 | Berge et al. |
| 7,030,137 | B2 | 4/2006 | Berge et al. |
| 7,973,050 | B2 | 7/2011 | Guiles et al. |
| 7,994,192 | B2 | 8/2011 | Guiles et al. |
| 2008/0108651 | A1 | 5/2008 | Guiles et al. |
| 2008/0146609 | A1 | 6/2008 | Guiles et al. |
| 2008/0227808 | A1 | 9/2008 | Guiles et al. |

FOREIGN PATENT DOCUMENTS

| EP | 0785268 | 7/1997 |
| WO | WO 99/55677 | 11/1999 |
| WO | WO 00/21949 | 4/2000 |
| WO | WO 00/71524 | 11/2000 |
| WO | WO 2004/052288 | 6/2004 |
| WO | WO 2004/069196 | 8/2004 |
| WO | WO 2004/078119 | 9/2004 |
| WO | WO 2008/039639 | 4/2008 |
| WO | WO 2008/039640 | 4/2008 |
| WO | WO 2008/039641 | 4/2008 |
| WO | WO 2008/039642 | 4/2008 |

OTHER PUBLICATIONS (Critchley, Antimicrobial Agents and Chemotherapy, Oct. 2005, p. 4247-52).*
Elsayed, J of Clin Microbiology, Sep. 2004, 4390-92.*
Smith-Slates, Pediatrics, 2006, e796-e805), Jiang (J of Clin Microbiol, 2009, 1599-1601.*
Jiang (J of Clin Microbiol, 2009, 1599-1601).*
Hall et al., Am J Dis Child (1035) 49:390-402, 1935.
Bartlett et al., Gastroenterology (1978) 75:778-782.
Loo et al., N. Engl. J Med. (2005) 353:2442-2449.
Thomas et al., J Antimicrob Chemother (2003) 51:1339-1350.
Bartlett and Perl, N. Engl. J Med (2005) 353:2503-2505.
Clabots et al., J Infect. Dis., 166, 561-567, 1992.
McFarland et al., N. Engl. J Med., 320, 204-210, 1989.
Teasley et al., Lancet (1983) 2:1043-1046.
Wilcox and Spencer, J Hosp. Infect. (1992) 22:85-92.
U.S. Appl. No. 10/729,416, filed Dec. 5, 2003, Berge et al.
U.S. Appl. No. 11/223,327, filed Sep. 9, 2005, Berge et al.
Pepin et al., Clin Infect Dis (2005) 40:1591-1597).
Hurdle et al Antimicrob Agents Chemother Dec. 2005;49(12):4821-33.
Lyerly et al., Clin Microbiol Rev. (1988) 1:1-18.
Voth et al., Clin Microbiol Rev (2005) 18:247-363.
Barker (1995) "An Easy Synthesis of 3-Amino- and 3-Nitrothiophene" Synthetic Comm. 25:3729-3734.
Brown et al (2003) "Horizontal Transfer of Drug-Resistant Aminoacyl-Transfer-RNA Synthesis of Anthrax and Gram-Positive Pathogens" EMBO Reports 4(7):692-698.
EP Supplemental Search Report (Mar. 21, 2011) received in EP Application No. 07842226.8.
Fleischmann et al., *Science* 269:496-512 (1995).
Gentry et al (2003) "Variable Sensitivity to Bacterial Methionyl-tRNA Synthetase inhibitors Reveals Subpopulations of *Streptococcus pneumoniae* with Two Distinct methionyl-tRNA Synthetase Genes" Antimicrobial Agents and Chemotherapy 47(6):1784-1789.
Jarvest et al (2002) "Nanomolar Inhibitors of *Staphylococcus aureus* Methionyl tRNA Synthetase with Potent Antibacterial Activity Against Gram-Positive Pathogens" Journal of Medicinal Chemistry 45(10):1959-1962.
Jarvest et al (2003) "Conformational Restriction of Methionyl tRNA Synthetase Inhibitors Leading to Analogues with Potent Inhibition and Excellent Gram-Positive Antibacterial Activity" Bioorganic & Medicinal Chemistry Letters 13:1265-126.
Jarvest et al (2004) "Definition of the Heterocyclic Pharmacophore of Bacterial Methionyl tRNA Synthetase Inhibitors: Potent Antibacterially Active Non-Quinolone Analogues" Bioorganic & Medicinal Chemistry Letters 14:3937-394.
Kim and Lee (2003) "3-D-QSAR Study and Molecular Docking of Methionyl-tRNA Synthetase Inhibitors" Bioorganic & Medicinal Chemistry 11:5325-533.

(Continued)

*Primary Examiner* — Sreeni Padmanabhan
*Assistant Examiner* — Uma Ramachandran
(74) *Attorney, Agent, or Firm* — Swanson & Bratschun, L.L.C.

(57) ABSTRACT

Methionyl tRNA synthetase inhibitors (MetRS) are provided for use in therapy as antibacterial agents in *Clostridium* based infection.

2 Claims, No Drawings

(56) References Cited

OTHER PUBLICATIONS

King (1994) "Bioisosteres, Conformational Restriction, and Prodrugs-Case History: An Example of a Conformational Restriction Approach" Medicinal Chemistry: Principle and Practice:206-22.

Lin et al (2001) "Principles and Applications of Asymmetric Synthesis" Wiley-Interscience pp. 1-1.

Office Action mailed Sep. 15, 2010 with respect to U.S. Appl. No. 11/853,589.

Office Action mailed Sep. 23, 2010 with respect to U.S. Appl. No. 11/853,477.

Office Action mailed Sep. 15, 2010 with respect to U.S. Appl. No. 11/853,314.

Smith M.B., (2001) "The Cahn-Ingold-Prelog System" March J, March's Advanced Org. Chem., 5th ed., Wiley-Interscience, NY, p. 139-143.

Notice of Allowance mailed May 13, 2011 with respect to U.S. Appl. No. 11/853,477.

Notice of Allowance mailed May 18, 2011 with respect to U.S. Appl. No. 11/853,314.

\* cited by examiner

METHODS AND COMPOUNDS FOR TREATMENT OF CLOSTRIDIUM BASED INFECTION

RELATED APPLICATIONS

This application claims the benefit under 35 U.S.C. §119, of U.S. Provisional Patent Application Ser. No. 60/826,957 entitled "Methods and Compositions For Treatment of *Clostridium* Based Infection," filed Sep. 26, 2006, and incorporated by reference herein in its entirety. This application is related to U.S. patent applications: ENANTIOMERIC COMPOUNDS WITH ANTIBACTERIAL ACTIVITY, Ser. No. 60/826,940, filed Sep. 26, 2006 and to corresponding US non-provisional and PCT applications filed on Sep. 11, 2007; SUBSTITUTED THIENOPYRIDONE COMPOUNDS WITH ANTIBACTERIAL ACTIVITY, Ser. No. 60/826,945 filed Sep. 26, 2006 and corresponding US non-provisional and PCT applications filed on Sep. 11, 2007; and SUBSTITUTED PHENYLETHER-THIENOPYRIDONE COMPOUNDS WITH ANTIBACTERIAL ACTIVITY, Ser. No. 60/826,954 filed Sep. 26, 2006 and corresponding US non-provisional and PCT applications filed on Sep. 11, 2007. The current application is also related to U.S. Pat. No. 6,943,175, filed Dec. 5, 2003, U.S. Pat. No. 7,030,137, filed Feb. 27, 2004, and to U.S. patent application Ser. Nos. 10/729,416, filed Dec. 5, 2003 and 11/223,327, filed Sep. 9, 2005. Each of the above referenced applications and patents are incorporated by reference herein for all purposes.

TECHNICAL FIELD

The present invention relates to the use of bacterial methionyl tRNA synthetase (MetRS) inhibitors as antibacterial agents in the treatment of *Clostridium* based infection, and in particular to the use of MetRS inhibitors in the treatment of *Clostridium difficile* infection.

BACKGROUND OF THE INVENTION

*Clostridium* bacteria are a spore forming family of Gram-positive anaerobes, including *Clostridium(C) perfringens, C. tetani, C. botulinum* and *C. difficile*. The *Clostridium* family of bacteria have been associated with a number of human maladies; in particular *C. difficile* has been shown to be the major causative agent for pseudomembraneous colitis and toxic megacolon as well as other antibiotic associated diarrheas (AAD).

*C. difficile* was first isolated in 1935 from intestinal flora of newborn infants (Hall et al., Am J Dis Child (1935) 49:390-402). In 1978, *C. difficile* was identified as the primary causative agent of pseudomembraneous colitis (now referred to as *C. difficile* associated diarrhea (CDAD)) (Bartlett et al., Gastroenterology (1978) 75:778-782), an inflammatory condition of the large intestine characterized by diarrhea that ranges in severity from mild to fulminant and is associated with the appearance of distinct raised plaques and neutrophil accumulation in the lumen of the intestinal lining. In general, these *C. difficile* related diarrheas result in about 10% to 30% mortality, especially in the elderly and in particular the elderly in hospital settings.

*C. difficile* has proven quite difficult to eradicate, especially in the hospital or healthcare setting (Loo et al., N. Engl. J. Med. (2005) 353:2442-2449; Thomas et al., J Antimicrob Chemother (2003) 51:1339-1350). In fact, whereas only 1-3% of healthy adults are carriers of *C. difficile*, hospitalization increases the risk of colonization to as high as 50% in a manner directly proportional to the length of hospitalization (Bartlett and Perl, N. Engl. J. Med. (2005) 353:2503-2505; Clabots et al., J. Infect. Dis., 166, 561-567, 1992; McFarland et al., N. Engl. J. Med., 320, 204-210, 1989). *C. difficile* infection is therefore a prevalent and growing problem within the healthcare industry.

There are few drugs that have shown promise in the treatment of CDAD. Presently, only vancomycin (125 mg four times a day for a period of seven to fourteen days) is approved by the FDA for treatment of CDAD. Metronidazole (250 mg three times a day for a period of seven to fourteen days) is also used extensively in clinical practice following early reports of its efficacy in CDAD (Teasley et al., Lancet (1983) 2:1043-1046; Wilcox and Spencer, J. Hosp. Infect. (1992) 22:85-92). However, recent studies have noted relatively high and growing incidence of treatment failure and relapse following metronidazole therapy (Pepin et al., Clin Infect Dis (2005) 40:1591-1597). Widespread vancomycin use in the treatment of CDAD (as well as other more common infections) has raised concerns about selection for vancomycin resistant strains of *C. difficile* and other bacteria. These concerns have led to proposals for first-line metronidazole use, with vancomycin being reserved for patients who are severely ill or have failed prior therapy. Bartlett et al., supra. Overall, options for the treatment of CDAD are limited, and there is a need in the industry for the development of new agents to address this prevalent and growing problem.

Amino acyl tRNA synthetases represent a promising platform for the development of new antibacterial agents with little cross-resistance to currently marketed antibiotics (Hurdle et al Antimicrob Agents Chemother. 2005 December; 49(12):4821-33). These synthetases play an essential role in protein synthesis by charging tRNA molecules with their corresponding amino acid so that the amino acid can be delivered to the ribosome for protein synthesis. In most bacteria, including *C. difficile*, a decrease in the ratio of charged to uncharged tRNA triggers a physiological reaction called the "stringent response." The stringent response induces a down-regulation of the synthesis of rRNA and tRNA, thereby inhibiting protein synthesis and ultimately the attenuation of bacterial growth. As such, amino acyl tRNA synthetases represent a potentially new molecular target for antibacterial agents. The inhibitor mupirocin (an inhibitor of isoleucyl tRNA synthetase) was released as a topical antibiotic in the treatment of *S. aureus* and *S. pyogenes* infections. Mupirocin is produced by the organism *Pseudomonas fluorescens*, and is an antibacterial agent used as the active ingredient in the product Bactroban®, marketed by GlaxoSmithKline.

Against this backdrop the present invention has been developed.

DETAILED DESCRIPTION OF THE INVENTION

*Clostridium:*

*Clostridium* is a spore-forming, anaerobic, Gram-positive bacillus. *Clostridium* genus members include common free-living bacteria as well as several important pathogens: *Clostridium(C) perfringens, C. tetani, C. botulinum* and *C. difficile. C. perfringens* is a common bacterium found in soil, often having a role in food poisoning and gas gangrene; *C. tetani* is the causative agent in tetanus or lockjaw (a disease largely eradicated in the industrialized world due to the tetanus vaccine); *C. botulinum* is the causative agent in botulism, found typically in soil or fish; and *C. difficile* is a bacterium associated with severe infections of the colon, showing an ability to flourish in the gut while other bacterium are eliminated during antibiotic treatment.

Methods and compounds of the invention are useful in the treatment of each of these *Clostridium* bacterium infections. However, because of its relative increasing prevalence in causation of disease, this case and its methods are directed toward *C. difficile*. Note, however, that inhibitors of the present invention are useful in the eradication and treatment of any of the *Clostridium* based infections.

Generally speaking, *C. difficile* infection results in extreme inflammation of the infected hosts' intestinal lining as caused by a group of secreted toxins. Clostridial toxins A and B (TcdA and TcdB) have been shown as the likely causative agents in this manner (Lyerly et al., Clin. Microbiol. Rev. (1988) 1:1-18; Voth et al., Clin Microbiol Rev (2005) 18:247-363). TcdA and B are structurally and functionally related to glycosyltransferases which enter the intestinal epithelial cells by receptor-mediated endocytosis and catalyze UDP glucose-mediated glucosylation of small GTPases in the Ras superfamily (like Rho, Rac and Cdc42). Glucosylation of these Ras superfamily GTPases results in their irreversible inactivation and consequent actin condensation, cell rounding, membrane blebbing, disruptions of tight junctions between cells and ultimately cell death by apoptosis.

In the *C. difficile* genome, TcdA and B are encoded on a 19.6 kb pathogenicity locus (PaLoc). Also encoded on PaLoc are TcdC and D, the putative negative and positive regulators of TcdA and B expression. In addition, TcdE, a cell permeabilizing factor is encoded on PaLoc, a factor involved in the release of the two toxins.

In addition to TcdA and B, several strains of *C. difficile* encode a binary toxin encoded by cdtA and cdtB genes. These two genes are not encoded on the PaLoc. The proteins encoded by these genes, CDTa and CDTb, form a two-component toxin in which CDTb mediates receptor-mediated endocytosis and CDTa modifies actin filaments through its ADP-ribosyltransferase activity. CDTa and CDTb proteins are more than 80% identical in sequence with the corresponding components of the iota toxin from *C. perfringens*.

Vancomycin is the only antibiotic currently approved by the FDA for the treatment of *C. difficile* based infections. Metronidazole is also extensively used in clinical practice following early reports of its efficacy in CDAD. However, recent studies have noted a relatively high and growing incidence of treatment failure and relapse following metronidazole therapy (Pepin et al., Clin Infect Dis (2005) 40:1591-1597). Widespread vancomycin use, however, raises concerns about selection for vancomycin being reserved for patients who are severely ill or have failed prior therapy. Overall, other treatment options have not been developed for treatment of *C. difficile* based disease.

Therefore, one aspect of the present invention is directed at developing new therapies for the treatment of *Clostridium* based infection. Compounds and methods of the present invention accomplish these interrelated goals.

Methionyl tRNA Synthetase:

Amino acyl tRNA synthetases represent a promising platform for the development of new antibacterial agents. These enzymes play an essential role in protein synthesis by charging tRNA molecules with their corresponding amino acid so that the ribosome can perform protein synthesis. In most bacteria, including pathogens, a decrease in the ratio of charged to uncharged tRNA triggers a physiological reaction called the "stringent response." The stringent response induces a down-regulation of rRNA and tRNA, which results in the attenuation of bacterial growth.

Methionyl tRNA synthetase (MetRS) enzyme is a novel and unexploited target for treatments directed at *Clostridium* based infections, especially infections caused by *C. difficile*. Phylogenetic analysis of MetRS enzymes reveals that it falls into either a type I or type II class, where Gram-positive bacteria generally show a type I characteristic.

Therefore, the present invention targets MetRS enzymes. In preferred embodiments, the inhibitor compounds of the invention target MetRS enzymes and are particularly useful in the treatment of *Clostridium*, and more particularly, *C. difficile* caused disease.

MetRS Inhibitors:

The present invention provides inhibitors of *Clostridium* derived MetRS. Any inhibitor targeted at the MetRS enzyme is within the scope of the present invention, although a series of illustrative compounds are provided herein. The present invention teaches that inhibitors directed at the MetRS enzyme are extremely potent antibacterial agents in the treatment of *Clostridium* bacterium and in particular *C. difficile*.

A number of potent inhibitors of *Clostridium* derived MetRS are provided. These compounds have been identified as potent antibacterial agents useful in the treatment of *Clostridium* infection, and in particular *C. difficile* infection.

Illustrative agents for use in the context of the present invention are described in co-pending U.S. patent applications entitled: ENATIOMERIC COMPOUNDS WITH ANTIBACTERIAL ACTIVITY; SUBSTITUTED THIENOPYRIDONE COMPOUNDS WITH ANTIBACTERIAL ACTIVITY; and SUBSTITUTED PHENYLETHER-THIENOPYRIDONE COMPOUNDS WITH ANTIBACTERIAL ACTIVITY; each having the same ownership as the present invention and each filed on the same day as the present disclosure. Each of these three cases is incorporated by reference herein for all purposes. In addition, inhibitors described within U.S. Pat. No. 6,943,175, filed Dec. 5, 2003 and U.S. Pat. No. 7,030,137, filed Feb. 27, 2004, U.S. patent application Ser. Nos. 10/729,416, filed Dec. 5, 2003, Ser. No. 11/223,327, filed Sep. 9, 2005, and PCT publications WO 00/71524, WO 2004/052288, WO 2004/078119, WO 2004/069196, and WO 99/55677 are all also incorporated by reference herein for all purposes.

In brief, illustrative compounds of the invention show excellent anti-*Clostridium* activity as determined by $IC_{50}$, $MIC_{90}$ and animal study data (see Examples 2-5). In addition, compounds of the invention inhibit growth and production of *C. difficile* toxin (Example 6) and reduced *C. difficile* spore formation (Example 7). In particular, illustrative compounds of the present invention are surprisingly potent inhibitors of MetRS and of *C. difficile* growth and show the capability to treat animals having a *C. difficile* infection. MetRS inhibitors have good activity against *C. difficile* and limited activity against other "friendly" intestinal strains. The ability of MetRS inhibitors to inhibit spore formation and toxin production may be useful in reducing outbreaks, relapse and reinfection rates. The combination of these benefits shows the utility of methods and compounds of the present invention.

In a number of the embodiments, inhibitors of the invention have a general structure as shown in formula (I):

$$LHS-X-NH-\frown-Y-NH-Z-RHS \quad (I)$$

in which:

X is the left hand side (LHS) substituent and is a substituted or unsubstituted aryl or heteroaryl group;

Z is the right hand side (RHS) substituent and has a substituted or unsubstituted aryl or heteroaryl group; and Y is a linker group having from one to six methylene groups in a straight chain and in which one or more methylene groups may have one or more $(C_{1-6})$ alkyl, $(C_{1-6})$alkoxy or $(C_{1-6})$alkylidenyl substituents.

Note that the linker:

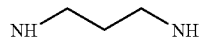

is preferred, providing an optimal spacing between the two aryl groups (noting that other similarly spaced linkers may be substituted).

In one embodiment, compounds of the present invention are shown in formula (II):

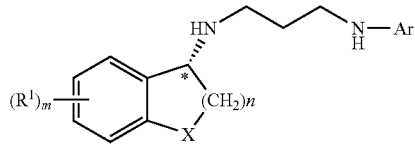

in which:

Ar is the right hand side (RHS) substituent and has a substituted or unsubstituted aryl or heteroaryl group;

X is selected from the group consisting of NH, O, S, SO, $SO_2$, or $CH_2$;

n is 1, 2 or 3;

* indicates an asymmetric carbon atom, wherein when n is 2 or 3, then * is R configuration; wherein when n is 1 and X is $CH_2$, then * is R configuration; and wherein when n is 1 and X is selected from the group consisting of NH, O, S, SO, or $SO_2$, then * is S configuration;

m is 0, 1, 2, 3, or 4; and $R^1$ is independently selected from halo, cyano, hydroxyl, $(C_{1-6})$alkyl (optionally substituted by halo, hydroxyl, amino, carboxy, or $(C_{1-6})$alkoxycarbonyl), $(C_{3-7})$cycloalkyl, $C_{(1-6)}$ alkoxy, amino, mono- or di-$(C_{1-6})$alkylamino, acylamino, carboxy, $(C_{1-6})$alkoxycarbonyl, carboxy$(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl and heterocyclic.

Preferred embodiments of the invention are those compounds of the formula (IIa) and (IIb):

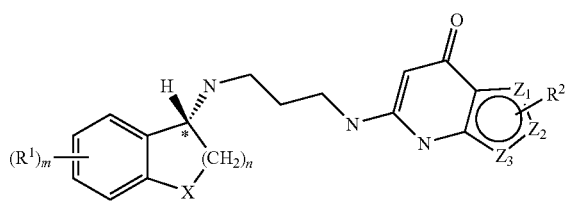

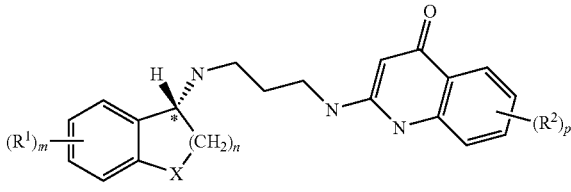

in which:

X is selected from the group consisting of NH, O, S, SO, $SO_2$, or $CH_2$;

n is 1, 2 or 3;

* indicates an asymmetric carbon atom, wherein when n is 2 or 3, then * is R configuration; wherein when n is 1 and X is $CH_2$, then * is R configuration; and wherein when n is 1 and X is selected from the group consisting of NH, O, S, SO, or $SO_2$, then * is S configuration;

$R^1$ is independently selected from halo, cyano, hydroxyl, $(C_{1-6})$alkyl (optionally substituted by halo, hydroxyl, amino, carboxy, or $(C_{1-6})$alkoxycarbonyl), $(C_{3-7})$cycloalkyl, $C_{(1-6)}$ alkoxy, amino, mono- or di-$(C_{1-6})$alkylamino, acylamino, carboxy, $(C_{1-6})$alkoxycarbonyl, carboxy$(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl and heterocyclic;

m is 0, 1, 2, 3 or 4;

p is 0, 1, 2 or 3;

$R^2$ is independently selected from halo, cyano, hydroxyl, $(C_{1-6})$alkyl (optionally substituted by halo, hydroxyl, amino, carboxy, or $(C_{1-6})$alkoxycarbonyl), $(C_{3-7})$cycloalkyl, $C_{(1-6)}$ alkoxy, amino, mono- or di-$(C_{1-6})$alkylamino, acylamino, carboxy, $(C_{1-6})$alkoxycarbonyl, carboxy$(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl and heterocyclic; and when $Z_1$ is S, $Z_2$ and $Z_3$ are CH; when $Z_2$ is S, $Z_1$ and $Z_3$ are CH; and when $Z_3$ is S, $Z_1$ and $Z_2$ are CH.

Particularly preferred compounds of formula (IIa) and (IIb) include:

5-[3-((R)(−)-5,7-Dibromo-1,2,3,4-tetrahydro-naphthalen-1-ylamino)-propylamino]-4H-thieno[3,2-b]pyridine-7-one;

5-[3-((R)(+)-8-Bromo-6-chloro-chroman-4-ylamino)-propylamino]-4H-thieno[3,2-b]pyridine-7-one;

5-[3-((R)(+)-6,8-Dibromo-1,2,3,4-tetrahydro-quinolin-4-ylamino)-propylamino]-4H-thieno[3,2-b]pyridine-7-one;

5-[3-((R)(+)-6,8-Dibromo-chroman-4-ylamino)-propylamino]-4H-thieno[3,2-b]pyridine-7-one;

2-[3-((R)(+)-6,8-Dibromo-chroman-4-ylamino)-propylamino]-1H-quinolin-4-one; and

5-[3-((S)-5,7-Dibromo-benzofuran-3ylamino)-propylamino]-4H-thieno[3,2-b]pyridine-7-one.

It will be appreciated that certain compounds of the present invention may comprise one or more chiral centers so that compounds may exist as stereoisomers, including diastereoisomers and enantiomers. Embodiments of the invention cover all such stereoisomers, and mixtures thereof, including racemates and mixtures having an enantiomeric excess of one of the enantiomers.

Another embodiment of the present invention provides compounds of formula (III):

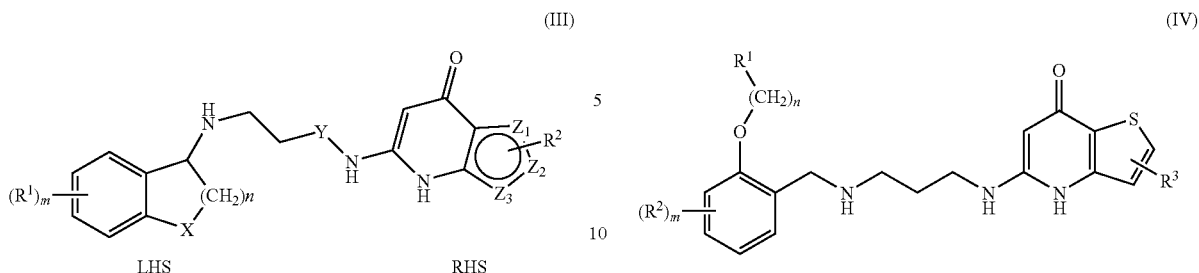

in which:

R¹ is selected from halo, cyano, hydroxyl, ($C_{1-6}$)alkyl (optionally substituted by halo, hydroxyl, amino, mono to perfluoro($C_{1-3}$)alkyl, carboxy, or ($C_{1-6}$)alkoxycarbonyl), ($C_{3-7}$) cycloalkyl, ($C_{1-6}$)alkoxy, amino, mono- or di-($C_{1-6}$) alkylamino, acylamino, carboxy, ($C_{1-6}$) alkoxycarbonyl, carboxy($C_{1-6}$)alkyloxy, ($C_{1-6}$)alkylthio, ($C_{1-6}$)alkylsulphanyl, ($C_{1-6}$) alkylsulphonyl, sulphamoyl, mono- and di-($C_{1-6}$) alkylsulphamoyl, carbamoyl, mono- and di-($C_{1-6}$) alkylcarbamoyl, and heterocyclyl;

Y is a linker group having from one to six methylene groups in a straight chain and in which one or more methylene groups may have one or more ($C_{1-6}$) alkyl, ($C_{1-6}$)alkoxy or ($C_{1-6}$)alkylidenyl substituents;

R² is selected from halo, cyano, hydroxyl, ($C_{1-6}$)alkyl (optionally substituted by halo, hydroxyl, amino, mono to perfluoro($C_{1-3}$)alkyl, carboxy, or ($C_{1-6}$)alkoxycarbonyl), ($C_{3-7}$) cycloalkyl, ($C_{1-6}$)alkoxy, amino, mono- or di-($C_{1-6}$) alkylamino, acylamino, carboxy, ($C_{1-6}$) alkoxycarbonyl, carboxy($C_{1-6}$)alkyloxy, ($C_{1-6}$)alkylthio, ($C_{1-6}$)alkylsulphanyl, ($C_{1-6}$)alkylsulphonyl, sulphamoyl, mono- and di-($C_{1-6}$) alkylsulphamoyl, carbamoyl, mono- and di-($C_{1-6}$) alkylcarbamoyl, and heterocyclyl;

when $Z_1$ is S, $Z_2$ and $Z_3$ are CH; when $Z_2$ is S, $Z_1$ and $Z_3$ are CH; when $Z_3$ is S, $Z_1$ and $Z_2$ are CH;

X is NH, S, SO, $SO_2$, O or $CH_2$;

m is 0 or an integer from 1 to 4; and n is one, two or three.

Preferred compounds of formula (III) include:

5-[3-(6,8-Dibromo-1,2,3,4-tetrahydro-quinolin-4-ylamino)-propylamino]-4H-thieno[3,2-b]pyridin-7-one;

5-[3-(6,8-Dibromo-chroman-4-ylamino)-propylamino]-4H-thieno[3,2-b]pyridin-7-one;

5-[3-(8-Bromo-6-chloro-chroman-4-ylamino)-propylamino]-4H-thieno[3,2-b]pyridin-7-one;

5-[3-(6-Chloro-8-iodo-chroman-4-ylamino)-propylamino]-4H-thieno[3,2-b]pyridin-7-one;

5-[3-(6-Bromo-8-chloro-chroman-4-ylamino)-propylamino]-4H-thieno[3,2-b]pyridin-7-one;

5-[3-(6-Bromo-8-chloro-1,2,3,4-tetrahydro-quinolin-4-ylamino)-propylamino]-4H-thieno[3,2-b]pyridin-7-one;

5-[3-(8-Bromo-6-chloro-1,2,3,4-tetrahydro-quinolin-4-ylamino)-propylamino]-4H-thieno[3,2-b]pyridin-7-one;

5-[3-(8-Bromo-6-methylsulfanyl-chroman-4-ylamino)-propylamino]-4H-thieno[3,2-b]pyridin-7-one; and 5-[3-(6-Bromo-8-fluoro-1,2,3,4-tetrahydro-quinolin-4-ylamino)-propylamino]-4H-thieno[3,2-b]pyridin-7-one.

Another embodiment of the invention provides compounds of formula (IV):

in which:

R¹ is selected from the group consisting of aryl and heteroaryl groups, including but not limited to substituted and unsubstituted benzene, toluene, phenol, anisole, thiazole, thiazolidine and pyridine, alkenes, imines, and other like substituents;

R² is independently selected from halo, cyano, hydroxyl, ($C_{1-6}$)alkyl (optionally substituted by halo, hydroxyl, amino, carboxy, or ($C_{1-6}$) alkoxycarbonyl), ($C_{1-6}$) cycloalkyl, ($C_{1-6}$) alkoxy, amino, mono- or di-($C_{1-6}$)alkylamino, acylamino, carboxy, ($C_{1-6}$)alkoxycarbonyl, carboxy($C_{1-6}$)alkyloxy, ($C_{1-6}$)alkylthio, ($C_{1-6}$)alkylsulphinyl, ($C_{1-6}$)alkylsulphonyl, sulphamoyl, mono- and di-($C_{1-6}$)alkylsulphamoyl, carbamoyl, mono- and di-($C_{1-6}$)alkylcarbamoyl, and heteroxy;

R³ is selected from a halo, ($C_{1-3}$)alkyl, ($C_{2-3}$)alkenyl, ($C_{2-3}$)alkynyl or other like substituents;

n is one, two or three; and m is 0, 1, 2 or 3.

Preferred compounds of formula (IV) include:

5-{3-[3-Bromo-5-methylsulfanyl-2-(2-pyridin-3-yl-ethoxy)-benzylamino]-propylamino}-4H-thieno[3,2-b]pyridine-7-one;

5-(3-{3-bromo-5-methylsulfanyl-2-[2-(4-methyl-thiazol-5-yl)-ethoxyl]-benzylamino}-propylamino)-4H-thieno[3,2-b]pyridine-7-one;

5-[3-(3-bromo-5-methylsulfanyl-2-phenethyloxy-benzylamino)-propylamino]-4H-thieno[3,2-b]pyridine-7-one;

5-(3-{3,5-Dibromo-2-[2-(4-methyl-thiazol-5-yl)-ethoxyl]-benzylamino}-propylamino)-4H-thieno[3,2-b]pyridine-7-one;

5-{3-[3,5-Dibromo-2-(2-pyridin-3-yl-ethoxy)-benzylamino]-propylamino}-4H-thieno[3,2-b]pyridine-7-one;

5-(3-{3,5-Dibromo-2-[2-(4,5-dimethyl-thiazol-2-yl)-ethoxy]-benzylamino}-propylamino)-4H-thieno[3,2-b]pyridine-7-one;

5-[3-(3,5-Dibromo-2-phenethyloxy-benzylamino)-propylamino]-4H-thieno[3,2-b]pyridine-7-one;

5-{3-[3,5-Dibromo-2-(3-pyridin-3-yl-propoxy)-benzylamino]-propylamino}-4H-thieno[3,2-b]pyridine-7-one;

5-(3-{3,5-Dibromo-2-[2-(3,4-dichloro-phenyl)-ethoxy]-benzylamino}-propylamino)-4H-thieno[3,2-b]pyridine-7-one;

5-(3-{3,5-Dibromo-2-[2-(4-methoxy-phenyl)-ethoxy]-benzylamino}-propylamino)-4H-thieno[3,2-b]pyridine-7-one;

5-{3-[3,5-Dibromo-2-(2-p-tolyl-ethoxy)-benzylamino]-propylamino}-4H-thieno[3,2-b]pyridine-7-one;

5-3-{3,5-Dibromo-2-[2-(fluoro-phenyl)-ethoxy]-benzylamino}-propylamino)-4H-thieno[3,2-b]pyridine-7-one;

5-(3-{3,5-Dibromo-2-[2-(4-chloro-phenyl)-ethoxy]-benzylamino}-propylamino)-4Hthieno[3,2-b]pyridine-7-one; and 5-{3-[3-Bromo-5-methylsulfanyl-2-(3-pyridin-3-yl-propoxy)-benzylamino]-propylamino}-4H-thieno[3,2-b]pyridine-7-one.

Another embodiment of the invention provides compounds of formula (V):

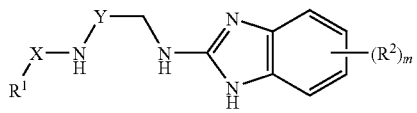

(V)

in which:

$R^1$ is an optionally substituted aryl or an optionally substituted heteroaryl ring;

$R^2$ is independently selected from halo, cyano, hydroxyl, $(C_{1-6})$alkyl, (optionally substituted by halo, hydroxy, amino, mono to perfluoro$(C_{1-3})$alkyl, carboxy, or $(C_{1-6})$ alkoxycarbonyl), $(C_{3-7})$cycloalkyl, $(C_{1-6})$alkoxy, amino, mono- or di-$(C_{1-6})$alkylamino, acylamino, carboxy, $(C_{1-6})$alkoxycarbonyl, carboxy$(C_{1-6})$alkyloxy, $(C_{1-6})$alkylthio, $(C_{1-6})$alkylsulphinyl, $(C_{1-6})$alkylsulphonyl, sulphamoyl, mono- and di$(C_{1-6})$alkylsulphamoyl, carbamoyl, mono- and di-$(C_{1-6})$alkylcarbamoyl, and heterocyclyl;

m is 0, 1, 2, or 3;

X is $CH_2$ or $CHR^3$ in which $R^3$ is $C_{(1-6)}$alkyl or is linked to the ortho position of an aryl or heteroaryl ring of $R^1$ to form a 5 to 7 membered ring optionally including oxygen or nitrogen as a ring atom; and Y is $(C_{1-3})$alkylene or $(C_{4-6})$cycloalkylene.

Another embodiment of the invention provides compounds of formula (VI):

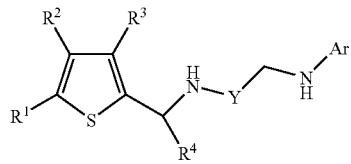

(VI)

in which:

$R^1$ is selected from the group consisting of Br, optionally fluoro-substituted $C_{(1-3)}$ alkyl, optionally fluoro-substituted $(C_{2-3})$alkenyl, and $(C_{2-3})$alkyl;

$R^2$ is a halogen, preferably Br;

$R^3$ is selected from the group consisting of $(C_{1-3})$alkyl, $(C_{2-5})$alkenyl, $(C_{2-3})$alkynyl;

$R^4$ is selected from the group consisting of H, and $(C_{1-3})$ alkyl;

Y is $C_{(1-3)}$alkyl; and

Ar is selected from the group consisting of substituted or unsubstituted heteroaryl imidiazole, substituted or unsubstituted quinolone, substituted or unsubstituted benzimidazole, substituted or unsubstituted fused heteroaryl pyridone, substituted or unsubstituted fused aryl pyrimidone, or substituted or unsubstituted fused heteroaryl pyrimidone.

Another embodiment of the invention provides compounds of formula (VII):

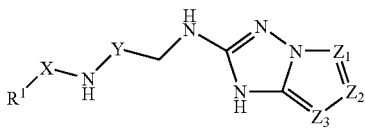

(VII)

in which:

$R^1$ is an optionally substituted aryl or an optionally substituted heteroaryl ring;

X is $CH_2$ or $CHR^3$ in which $R^3$ is $C_{(1-6)}$alkyl or is linked to the ortho position of an aryl or heteroaryl ring of $R^1$ to form a 5 to 7 membered ring optionally including oxygen or nitrogen as a ring atom;

Y is $C_{(1-3)}$alkylene or $C_{(4-6)}$cycloalkylene; and $Z_1$, $Z_2$ and $Z_3$ is each independently selected from N or $CR_4$ in which $R_4$ is hydrogen or a substituent selected from halogen, cyano, $(C_{1-6})$alkyl, mono- to per-fluoro$(C_{1-3})$ alkyl, $(C_{3-7})$cycloalkyl, $(C_{2-6})$alkenyl, $(C_{1-6})$alkoxy, $(C_{2-6})$alkenoxy, arylC$_{(1-6)}$alkoxy, halo$(C_{1-6})$ alkyl, hydroxyl, amino, mono- or di-$(C_{1-6})$alkylamino, acylamino, nitro, carboxy, $(C_{1-6})$ alkoxycarbonyl, $(C_{1-6})$alkenyloxycarbonyl, $(C_{1-6})$alkoxycarbonyl$(C_{1-6})$alkyl, carboxy$(C_{1-6})$ alkyl, $(C_{1-6})$alkylcarbonyloxy, carboxy$(C_{1-6})$alkyloxy, $(C_{1-6})$alkoxycarbonyl $(C_{1-6})$alkoxy, $C_{(1-6)}$ alkylthio, $(C_{1-6})$alkylsulphinyl, $(C_{1-6})$ alkylsulphonyl, sulphamoyl, mono- and di-$(C_{1-6})$-alkylsulphamoyl, carbamoyl, mono- and di-$(C_{1-6})$ alkylcarbamoyl, and heterocyclyl.

Another embodiment of the invention provides compounds of formula (VIII):

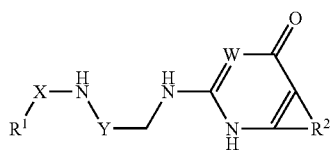

(VIII)

in which:

W is CH and $R^2$ is the residue of a 5 or 6-membered heteroaryl ring, or W is N and $R^2$ is the residue of an 5 or 6-membered heteroaryl ring or an aryl ring, which heteroaryl or aryl ring is optionally substituted with from one to three substituents selected from halo, cyano, hydroxyl, $(C_{1-6})$alkyl (optionally substituted by halo, hydroxyl, amino, mono, to perfluoro$(C_{1-3})$ alkyl, carboxy, or $(C_{1-6})$alkoxycarbonyl, $(C_{3-7})$cycloalkyl, $C_{(1-6)}$alkoxy, amino, mono- or di-$(C_{1-6})$ alkoxycarbonyl, acylamino, carboxy, $(C_{1-6})$alkoxycarbonyl, carboxy$(C_{1-6})$alkyloxy, $(C_{1-6})$alkythio, $(C_{1-6})$alkylsulphamoyl, carbamoyl, mono- and di-$(C_{1-6})$alkycarbamoyl, and heterocyclyl;

$R^1$ is an optionally substituted aryl or an optionally substituted heteroaryl ring;

X is $CH_2$ or $CHR^3$ in which $R^3$ is C(1-6)alkyl or $R^3$ may be linked to the ortho position or an aryl or heteroaryl ring of $R^1$ to form a 5 to 7 membered ring optionally including oxygen or nitrogen as a ring atom; and Y is $C_{(1-3)}$alkylene or $C_{(4-6)}$cycloalkylene.

Another embodiment of the invention provides compounds of formula (IX):

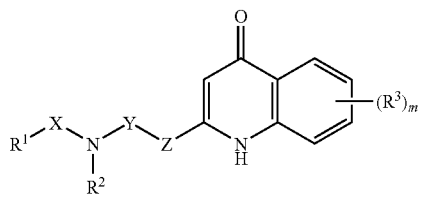 (IX)

in which:

R¹ is optionally substituted aryl or optionally substituted heteroaryl group;

R² is hydrogen, $C_{(1-6)}$alkyl, aryl $C_{(1-4)}$alkyl, aryl $C_{(2-4)}$ alkenyl or $C_{(1-6)}$ alkylcarbonyl;

R³ is selected from halo, cyano, hydroxyl, $(C_{1-6})$alkyl (optionally substituted by halo, hydroxyl, amino, mono to perfluoro$(C_{1-3})$alkyl, carboxy, or $(C_{1-6})$alkoxycarbonyl), $(C_{3-7})$ cycloalkyl, $C_{(1-6)}$alkoxy, amino, mono- or di-$(C_{1-6})$ alkoxycarbonyl, acylamino, carboxy, $(C_{1-6})$alkoxycarbonyl, carboxy$(C_{1-6})$alkyloxy, $(C_{1-6})$alkythio, $(C_{1-6})$alkylsulphamoyl, carbamoyl, mono- and di-$(C_{1-6})$alkycarbamoyl, and heterocyclyl;

m is 0 or an integer from one to three;

X is $CHR^4$ wherein $R^4$ is hydrogen, $C_{(1-6)}$alkyl or aryl, $C_{(2-4)}$alkylene, $C_{(3-4)}$ alkenylene or CO;

Y is a linker group having from two to six methylene groups in a straight chain and in which one or more methylene groups may have one or more $C_{(1-6)}$alkyl, $C_{(1-6)}$alkoxy, or $C_{(1-6)}$alkylidenyl substituents and in which chain 1,2- or 1,3- carbon atoms may be linked by a $C_{(2-3)}$alkyene or C3 alkenylene bridge;

R¹ and X or R¹ and R² may be linked by a polymethylene chain to form a 5 to 7 membered ring, optionally substituted by $C_{(1-6)}$alkyl;

X and R², X and Y or Y and R² may be linked by a polymethylene chain to form a 4 to 7 membered ring, optionally substituted by $C_{(1-6)}$alkyl; and Z is NH or O.

Finally, another embodiment of the invention provides compounds of formula (X):

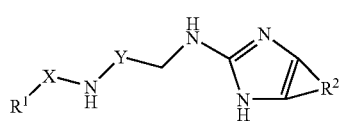 (X)

in which:

R¹ is an optionally substituted aryl or an optionally substituted heteroaryl ring;

R² is the residue of a 5 or 6-membered heteroaryl ring which is optionally substituted with from 1 to 3 substituents selected from halo, cyano, hydroxy, $(C_{1-6})$alkyl (optionally substituted by halo, hydroxy, amino, mono to perfluoro$(C_{1-3})$alkyl, carboxy or $(C_{1-6})$alkoxycarbonyl), $(C_{3-7})$ cycloalkyl, $(C_{1-6})$alkoxy, amino, mono- or di-$(C_{1-6})$alkylamino, acylamino, carboxy, $(C_{1-6})$alkoxycarbonyl, carboxy $(C_{1-6})$alkyloxy, $(C_{1-6})$alkylthio, $(C_{1-6})$alkylsulphinyl, $(C_{1-6})$ alkylsulphonyl, sulphamoyl, mono- and di-$(C_{1-6})$ alkylsulphamoyl, carbamoyl, mono- and di-$(C_{1-6})$ alkylcarbamoyl, and heterocyclyl;

X is $CH_2$ or $CHR^3$ in which $R^3$ is $C_{(1-6)}$alkyl or is linked to the ortho position of an aryl or heteroaryl ring of R¹ to form a 5 to 7 membered ring optionally including oxygen or nitrogen as a ring atom; and Y is $C_{(1-3)}$alkylene or $C_{(4-6)}$cycloalkylene.

Compounds of the invention can also be salts of the compounds shown in formulas (I)-(X). Salts may be formed from inorganic and organic acids. Representative examples of suitable inorganic and organic acids from which pharmaceutically acceptable salts of compounds of formulas (I)-(X) may be formed include: maleic, fumaric, benzoic, ascorbic, pamoic, succinic, bismethylene-salicylic, methanesulfonic, ethanedislufonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

When used herein, the term "alkyl" and similar terms such as "alkoxy" includes all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the terms "alkenyl" and "alkynyl" include all straight chain and branched isomers. Representative examples thereof include vinyl, ethynyl and 1-propynyl.

Preferred substituents for alkyl and alkenyl groups include, for example, and unless otherwise defined, halogen, cyano, azido, nitro, carboxy, $(C_{1-6})$alkoxycarbonyl, carbamoyl, mono- or di-$(C_{1-6})$alkylcarbamoyl, sulpho, sulphamoyl, mono- or di-$(C_{1-6})$ alkylsulphamoyl, amino, mono- or di-$(C_{1-6})$alkylamino, acylamino, ureido, $(C_{1-6})$alkoxycarbonylamino, 2,2,2-trichloroethoxycarbonylamino, aryl, heterocyclyl, hydroxy, $(C_{1-6})$alkoxy, acyloxy, oxo, acyl, 2-thienoyl, $(C_{1-6})$alkylthio, $(C_{1-6})$alkylsulphinyl, $(C_{1-6})$ alkylsulphonyl, hydroxyimino, $(C_{1-6})$alkoxyimino, hydrazino, hydrazono, benzohydroximoyl, guanidino, amidino and iminoalkylamino.

When used herein, the term "aryl" includes, unless otherwise defined, phenyl or naphthyl optionally substituted with up to five, preferably up to three substituents.

When substituted, an aryl group may have up to three substituents. Preferred substituents for an aryl group include, for example, and unless otherwise defined, halogen, cyano, $(C_{1-6})$alkyl, mono to perfluoro$(C_{1-3})$alkyl, $(C_{3-7})$cycloalkyl, $(C_{2-6})$alkenyl, $(C_{1-6})$alkoxy, $(C_{2-6})$alkenoxy, arylC$_{(1-6)}$ alkoxy, halo$(C_{1-6})$alkyl, hydroxy, amino, mono- or di-$(C_{1-6})$ alkylamino, acylamino, nitro, carboxy, $(C_{1-6})$alkoxycarbonyl, $(C_{1-6})$alkenyloxycarbonyl, $(C_{1-6})$alkoxycarbonyl$(C_{1-6})$ alkyl, carboxy$(C_{1-6})$alkyl, $(C_{1-6})$alkylcarbonyloxy, carboxy $(C_{1-6})$alkyloxy, $(C_{1-6})$alkoxycarbonyl$(C_{1-6})$alkoxy, $(C_{1-6})$ alkylthio, $(C_{1-6})$alkylsulphinyl, $(C_{1-6})$alkylsulphonyl, sulphamoyl, mono- and di-$(C_{1-6})$-alkylsulphamoyl, carbamoyl, mono- and di-$(C_{1-6})$alkylcarbamoyl, and heterocyclyl.

When used herein, the term "heteroaryl" includes single or fused rings comprising up to four hetero-atoms in the ring selected from oxygen, nitrogen and sulphur. Preferably the heteroaryl ring comprises from 4 to 7, preferably 5 to 6, ring atoms. A fused heteroaryl ring system may include carbocyclic rings and need only include one heterocyclic ring.

When used herein, the term "heterocyclyl" includes aromatic and non-aromatic single or fused rings comprising up to four hetero-atoms in the ring selected from oxygen, nitrogen and sulphur. Suitably the heterocyclic ring comprises from 4 to 7, preferably 5 to 6, ring atoms. A fused heterocyclic ring system may include carbocyclic rings and need only include one heterocyclic ring.

When substituted, a heteroaryl or a heterocyclyl group may have up to three substituents. Preferred such substituents include those previously mentioned for an aryl group as well as oxo.

When used herein, the terms "halogen" and "halo" include fluorine, chlorine, bromine, and iodine and fluoro, chloro, bromo, and iodo, respectively.

The compounds of the present invention are suitably provided in substantially pure form, for example at least 50% pure, suitably at least 60% pure, advantageously at least 75% pure, preferably at least 85% pure, more preferably at least 95% pure, especially at least 98% pure. All percentages are calculated on a weight/weight basis. All impure or less pure forms of a compound according to the invention may, for example, be used in the preparation of more pure forms of the same compound or of a related compound (for example a corresponding derivative) suitable for pharmaceutical use.

Each of the compounds having formulas (I)-(X) are potent inhibitors of MetRS and have shown potent antibacterial activity against *Clostridium* based infections, and in particular against *C. difficile* based infections. Further, the compounds of the present invention are specific for bacterial MetRS and show little or no activity against mammalian MetRS, a good feature for use as an antibacterial agent.

A "compound of the invention" in context of the present invention means any compound having activity that possesses an $IC_{50}<64$ μM, an $MIC_{90}\leq16$ μg/mL, or an increased survival in an in vivo *Clostridium difficile* infection setting. In preferred embodiments the compounds of the invention have a structure as shown in formula (I) and in more preferred embodiments the compounds of the invention have a structure as shown in formulas (II)-(X) or of one of the compounds as described in one of the incorporated references herein.

The compounds of the present invention can be prepared by methods as described in the three co-pending applications that were incorporated by reference above or in one of the other references that have been incorporated by reference.

Methods For *C. difficile* Treatment:

Compounds of this invention (enumerated or incorporated herein by reference) are active against *Clostridium* bacterium, such as *C. perfringens, C. tetani, C. botulinum* and *C. difficile*. In preferred aspects, the compounds of the invention are particularly active against *C. difficile*, and can be used in relation to antibiotic resistant strains of *C. difficile*.

Ailments which may be treated by compounds of the invention include pseudomembraneous colitis, food poisoning, gas gangrene, tetanus or lockjaw, botulism, other severe infections of the colon, and toxic megacolon.

In addition, various other ailments may be targeted by methods and compositions of the present invention including: gastrointestinal tract infections, respiratory tract infections, otitis media, meningitis, endocarditis, skin and soft tissue infections in mammals such as humans, mastitis in cattle, and also respiratory infections in farm animals such as pigs and cattle. In each case the human or other mammal can be referred to as a "patient." Note that the term "treated" or "treatment" refers to an amelioration of an infection caused by *Clostridium* bacteria, or at least one discernible symptom thereof. Treated or treatment may also refer to an inhibition of the progression of an infection caused by *Clostridium* bacteria. Finally, the term treated or treatment may refer to delaying the onset of a *Clostridium* based bacterial infection in a human or non-human animal.

Accordingly, the present invention provides a method of treating *Clostridium* infection in mammals and in some embodiments humans, which method comprises administering a therapeutically effective amount of a compound of the invention to a mammal in need of such therapy. A therapeutically effective amount of a compound is an amount that will elicit a biologic or medical response in the mammal that is being treated by a healthcare professional (including doctors, nurses, physician assistants, veterinarians, etc). Note that the term mammal refers to any warm-blooded animal of the class Mammalia, including human, dog, cat, rat, horse, etc.

In another aspect of the invention, methods are provided for treating *Clostridium* infection in a mammal which methods comprise administering a prophylactically effective amount of a compound of the invention to the mammal in need of such therapy. A prophylactically effective amount of a compound of the invention is an amount that will prevent or inhibit affliction or mitigate affliction of a mammal with a *Clostridium* infection.

The present invention provides a pharmaceutical composition comprising a compound of the invention together with a pharmaceutically acceptable carrier or excipient. In preferred embodiments the pharmaceutical composition comprises a compound of formula (I) together with a pharmaceutically acceptable carrier or excipient and in more preferred embodiments the pharmaceutical composition comprises a compound of formula (II), (IIa), (IIb), (III), (IV), (V), (VI), (VII), (VIII), (IX), or (X) together with a pharmaceutically acceptable carrier or excipient.

The present invention further provides pharmaceutical compositions comprising combinations of two or more compounds of the invention together with a pharmaceutically acceptable carrier or excipient. For example, a pharmaceutical composition of the invention can include a compound of formula (I) and a compound of formula (II) in combination with the carrier or excipient. In addition, pharmaceutical compositions of the present invention can include other known antibiotic agents, for example, vancomycin or metronidazole. In addition, pharmaceutical compositions of the present invention can include other known agents, such as those that bind to toxins produced by *C. difficile*.

The present invention provides a method of treating bacterial infections in mammals, especially in humans and in domesticated mammals, which comprises administering a compound of the invention, or a composition according to the invention, to a patient in need thereof.

The invention further provides the use of compounds of the invention in the preparation of a medicament composition for use in the treatment of bacterial infections.

The compounds and compositions according to the invention may be formulated for administration in any convenient way for use in human or veterinary medicine, by analogy with other antibiotics.

The compounds and compositions according to the invention may be formulated for administration by any route, for example oral, topical, parenteral, or rectal. The compositions may, for example, be made up in the form of tablets, capsules, powders, granules, lozenges, creams, suppositories, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrolidone; fillers, for example lactose, sucrose, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminum stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavoring and color agents.

Compositions according to the invention intended for topical administration may, for example, be in the form of ointments, creams, lotions, eye ointments, eye drops, ear drops, impregnated dressings, and aerosols, and may contain appropriate conventional additives, including, for example, preservatives, solvents to assist drug penetration, and emollients in ointments, gels, and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, water being preferred. The compound, depending on the vehicle and concentration used, may be either suspended or dissolved in the vehicle. In preparing solutions, the compound may be dissolved in water for injection and filter-sterilized before being filled into a suitable vial or ampoule, which is then sealed. Advantageously, conventional additives including, for example, local anesthetics, preservatives, and buffering agents can be dissolved in the vehicle. In order to enhance the stability of the solution, the composition may be frozen after being filled into the vial, and the water removed under vacuum; the resulting dry lyophilized powder may then be sealed in the vial and a accompanying vial of water for injection may be supplied to reconstitute the liquid prior to use. Parenteral suspensions may be prepared in substantially the same manner except that the compound is suspended in the vehicle instead of being dissolved and sterilization cannot be accomplished by filtration. The compound may instead be sterilized by exposure to ethylene oxide before being suspended in the sterile vehicle. Advantageously, a surfactant or wetting agent is included in such suspensions in order to facilitate uniform distribution of the compound.

A compound or composition according to the invention may suitably be administered to the patient in an anti-*Clostridium* effective or prophylactic amount.

A composition according to the invention may suitably contain from 0.1% by weight, preferably from 10 to 60% by weight, of a compound according to the invention (based on the total weight of the composition), depending on the method of administration.

The compounds according to the invention may suitably be administered to the patient at a daily dosage of from 1.0 to 100 mg/kg of body weight. For an adult human (of approximately 70 kg body weight), from 50 to 3000 mg, for example about 1500 mg, of a compound according to the invention may be administered daily. Suitably, the dosage for adult humans is from 5 to 40 mg/kg per day. Higher or lower dosages may, however, be used in accordance with normal clinical practice.

When the compositions according to the invention are presented in unit dosage form, each unit dose may suitably comprise from 25 to 1000 mg, preferable from 50 to 500 mg, of a compound according to the invention.

Packs and Kits:

The invention also provides pharmaceutical packs or kits comprising one or more containers having one or more of the compounds of the invention. In addition, packs or kits can include instructions for use and any appropriate notices by a governmental agency regulating the manufacture, use or sale of the products. It is also envisioned that packs and kits of the invention can include other biologic agents useful in the treatment of *Clostridium* based infection.

EXAMPLES

The following examples are provided for illustrative purposes only and are not intended to limit the scope of the invention.

Example 1

Expression and Purification of MetRS

The following example illustrates expression and purification of *C. difficile* MetRS useful in the functional assays shown in Examples 2, 3 and 5.

Cloning of Over-producing Vector: N-terminally hexaHis-tagged *C. difficile* MetRS was amplified and cloned into pETcoco-2. The following primers were used to amplify DNA from genomic DNA: 5'-CTGCAGAGCTAGCAAAC-CGAGTTTTTATGTAAC-3' (forward) (SEQ ID NO:1), 5'-CTTTCTAAGCTTCTACTAACGAACCTCGGATCC-3' (reverse) (SEQ ID NO:2). Amplified DNA was treated with Sph1 and HindIII restriction endonucleases, which were heat-inactivated after digestion. The fragment was ethanol-precipitated and combined with pETcoco-2 vector (Novagen) that had been treated with the same enzymes plus shrimp alkaline phophatase. The fragments were ligated and the ligation mixture transformed into competent DH10 *E. coli*. Transformants were plated on F-medium plus glucose with 50 ug/ml ampicillin. Growth in glucose maintains the repressed state of the pBAD promoter driving expression of the replicator TrfA, thus maintaining low copy number. The resulting expression clone, pETcoco-Cdiff-MRS, was confirmed by sequencing of the insert in both directions.

Purification of *C. difficile* MetRS. The expression vector pETcoco-Cdiff-MRS was transformed into Rosetta DE3 expression strain and used to inoculate 4 liters of F media supplemented with 10 ug/mL chloramphenicol, 50 ug/mL ampicillin, 0.2% glucose. The culture was induced with 1 mM IPTG at OD 0.66. Cells were harvested 4 hours post-induction (yield=38 g cell pellet). Pelleted cells were lysed by adding 78 g of a 1:1 suspension of frozen cells (39 g cells) in Tris-sucrose which had been stored at −20° C. to 107.25 ml Tris-sucrose buffer that had been pre-warmed to 45° C. (2.75 ml/g of cells). To the stirred mixture, 1.95 ml of 0.5M 1,4-dithiothreitol (DTT) (0.05 ml/g of cells) and 9.75 ml of lysis buffer (2M NaCl, 0.3M spermidine in Tris-sucrose adjusted to pH 7.5) (0.25 ml/g of cells) was added. The pH of the slurry was tested with pH paper and adjusted to pH 8.0 by the addition of 50 ml of 2 M Tris base. Lysozyme (117 mg) was added in 20 ml of Tris-sucrose buffer (3 mg lysozyme/g of cells). The slurry was distributed into centrifuge bottles and incubated at 4° C. for 1 hour followed by incubation at 37° C. for 4 minutes. The insoluble cellular components were removed by centrifugation (23,000×g, 60 min, 4° C.). The recovered supernatant (192 ml) constituted Fraction I. Fraction I was loaded onto a 15 mL Ni-NTA column which was equilibrated in Load Buffer (50 mM Tris-HCl, pH 7.5, 10% glycerol, 40 mM KCl, 10 mM Imidazole, pH 6.8, and 7 mM beta mercaptoethanol). The column was washed with 10 column volumes of Wash Buffer (50 mM Tris-HCl, pH 7.5, 10% glycerol, 800 mM KCl, 20 mM Imidazole, pH 6.8, and 7 mM beta mercaptoethanol). The protein was eluted in 10 column volume gradient from Wash Buffer to Elution Buffer (50 mM Tris-HCl, pH 7.5, 10% glycerol, 40 mM KCl, 250 mM Imidazole, pH 6.8, and 7 mM beta mercaptoethanol) at 0.5 mL/min collecting 3 mL fractions. Fractions were collected and analyzed for protein by SDS-PAGE. Fractions were assayed in the *C. difficile* MetRS tRNA charging assay. Fractions containing peak activity were pooled to form Fraction II (60 mg at 1.3 mg/ml). Fraction II had a specific activity of $3.2 \times 10^5$ units per mg. The purity was estimated at greater than 97% based on densitometry of an SDS-PAGE gel stained with Coomassie blue.

Example 2

Compounds of the Present Invention have Potent Enzyme Activity Against MetRS

Compounds of the present invention were assayed to determine their ability to inhibit enzyme MetRS. All compounds were tested for antibacterial activity against a collection of non-repeat clinical isolates of *C. difficile*. The organisms were stored frozen in *Brucella* broth supplemented with 20% glycerol. The organisms were retrieved from the freezer and subcultured twice onto CDC agar to ensure purity and growth. The plates were incubated under anaerobic conditions for at least 24 hours. Bacterial colonies were examined for morphology; yellow color, ground glass texture and characteristic odor. The control organism tested was *Bacteroides fragilis* ATCC 25285.

Assays were performed as follows:

| Reaction Mix (per 1 ml) | | |
|---|---|---|
| Stock | Volume (μl) | Final Concentration |
| 100 mM Tris/Cl, pH 7.9 | 600 | 30 mM |
| 250 mM KCl | | 75 mM |
| 125 mM ATP | 40 | 2.5 mM |
| 250 mM MgCl$_2$ | 80 | 10 mM |
| 50 mM DTT | 80 | 2 mM |
| 1 mM Met (H-3 hot and cold) | 20 | 10 μM |
| Solid tRNA (Mixed *E. coli* MRE 600) | 4 mg/ml 180 | 2 mg/ml |
| H$_2$O | | |

10 × Inhibitor (0-100 μM) 5 μl per well 0-10 μM

Each reaction was started by adding 20 μl appropriately diluted pure enzyme (pre-incubated with inhibitor) to 25 μl reaction mix for 10 min at room temperature. The reaction is terminated by the addition of 150 μl 167 mM sodium citrate, pH 2.15 containing phosphodiesterase (PDE) SPA beads (0.833 mg/ml). The binding of the radiolabelled product to the bead brings the isotope into close enough proximity to allow radiation from the tritium to excite the scintillant within the bead. Any unbound radiolabel is not close enough to the scintillant to allow this energy transfer, so no signal is generated. Following termination of the reaction, plates are spun at 2500 rpm for 5 min in a Mistral 3000E plate centrifuge (or alternatively allowed to stand for 1 hour). The assay is conducted in 96-well Optiplates (Packard). Plates are counted on a TopCount. (Packard 96 well counter).

Reagents

Mixed *E. coli* MRE 600 tRNA and ATP were purchased from Boehringer-Mannheim, L-[methyl-$^3$H]methionine and phosphodiesterase scintillation proximity (SPA) beads from Amersham Pharmacia Biotech and other reagents from Sigma.

Results

MetRS inhibitor compounds had IC$_{50}$ values against *C. difficile* MetRS in the range <1.5-15 nM. All were highly selective with respect to the mammalian enzyme (no inhibition of rat MetRS up to 1 μM). This data indicates that the compounds of the present invention show strong selectivity toward inhibition of *C. difficile* MetRS, but have little or no inhibitory activity toward mammalian MetRS. MetRS inhibitors are competitive inhibitors of methionine and uncompetitive inhibitors of ATP.

Example 3

Compounds of the Present Invention Have Potent Antibacterial Activity Against *C. difficile*

MetRS inhibitor compounds were also assayed for their capacity to inhibit *C. difficile* growth. MIC$_{90}$ (minimum inhibition concentration required to inhibit the growth of 90% of *C. difficile*) was determined using standard agar based assays according to CLSI.

Organisms: All compounds were tested for antibacterial activity against a collection of non-repeat clinical isolates of *C. difficile*. The organisms were stored frozen in *Brucella* broth supplemented with 20% glycerol. The organisms were retrieved from the freezer and subcultured twice onto CDC agar to ensure purity and growth. The plates were incubated under anaerobic conditions for at least 24 hours. Bacterial colonies were examined for morphology; yellow color, ground glass texture and characteristic odor. The control organism tested was *Bacteroides fragilis* ATCC 25285.

Antimicrobial susceptibility testing: Antimicrobial susceptibility testing was conducted by the agar dilution method on *Brucella* agar supplemented with vitamin K$_1$, hemin and 5% laked sheep blood in accordance with CLSI guidelines (CLSI, M11-A2). The test compounds were serially diluted and added to molten supplemented *Brucella* agar. Drug free plates were inoculated before and after inoculation of each antimicrobial plate series and were used as growth controls. Anaerobic/aerobic growth controls were conducted on drug free plates after two sets of drug plates. Bacterial colonies were suspended in *Brucella* broth to a turbidity equal to that of a 0.5 McFarland standard and applied to a plate with a Steers replicator that delivered 10$^5$ CFU/spot. The plates were incubated under anaerobic conditions for 24 hours at 35° C.

prior to the reading of the results. The minimum inhibitory concentration (MIC) was the concentration that completely inhibited growth or caused a marked reduction in the appearance of growth compared to that of the drug-free growth control.

Results: $MIC_{90}$ for MetRS inhibitor compounds ranged from 0.25 to >32 µg/ml. These results indicate the potent activity of the compounds of the present invention against *C. difficile*, typically around 0.5 µg/ml. In addition, $IC_{50}$ data indicates that the compounds of the present invention are specific for *C. difficile*, showing little or no activity against mammalian MetRS. MetRS inhibitor compounds show potent activity against *C. difficile* and gram positive bacteria while sparing normal gut flora.

Example 4

Genus Members of *Clostridium* Show Strong MetRS Sequence Identity

The amino acid sequences for MetRS of *C. perfringens* (SEQ ID NO:3), *C. acetoburylicum* (SEQ IS NO:4), *C. tetani* (SEQ ID NO:5) and *C. difficile* (SEQ ID NO:6) are shown in Table 1:

TABLE 1

Alignment of *Clostridium* Family Member MetRS amino acid sequence

```
C.perfringens   -MCKKPYYITTPIYYPSTNLHIGNTYTTVAADAIARFKRLTGHEVMFLTGTDEHGQKIER   59 (SEQ ID NO:3)
C.acetobutylicum MSEKKKFYITTPIYYPSAKLHIGNTYTTVASDALVRFKRLQGYDAFMLTGTDEHGQKIQR   60 (SEQ ID NO:4)
C.tetani        -MNKKTFYITTPIYYPSAKLHIGNTYTTVAADALARFKRLTGHDVLFLTGTDEHGQKIQR   59 (SEQ ID NO:5)
C.difficile     -MSKPSFYVTTPIYYPSGGLHIGHTYSTVAADTIARFKRFCGYDVKFLTGTDEHGEKIQK   59 (SEQ ID NO:6)
                 *  :*:********  ****:**:***.*:..****:  *:.:  :********:**::

C.perfringens   IANEKGITPKEHVDEIVAGIKDLWKMMNISYDKFIRTTDDYHVKAVQEIFKKLYDQGDIY   119
C.acetobutylicum IAEDKGITPKAYVDEIVAGIKDLWKMMNISYDKFIRTTDEEHVKAVQKIVKKFYDNGDIY   120
C.tetani        VAEEKGLKPKEYLDNMVDSIKELWKSMNISYDKFIRTTDDYHIESVQKIFKKLYEQGDIY   119
C.difficile     KAIEQGMSEIEYLDGMIKDIKALWNTMDISYDDFIRTT-ERHTDIIQKIFTKLYEQGDIY   118
                 *  ::*:.     ::*  ::.**.**: *:****.***** : *  .:*:*..*:*::****

C.perfringens   KDSYEGLYCTPCESFWTETQLVNGN-CPDCGRPVEKAKEEAYFFKMSKYADRLIQYIEEH   178
C.acetobutylicum KSAYEGWYCTPCESFWTETQLVDGK-CPDCGRPVEKTKEEAYFFKMSKYADRLIKYIEDH   179
C.tetani        KGEYEGWYCTPCESFWTESQLDDHN-CPDCGRPVEKTKEEAYFFKMSKYADRLIKYIEEN   178
C.difficile     KGEYEGRYCTPCESFWTESQLLEGNKCPDCGRETYLVKEESYFFRLSKYEDRLKELFKDD   178
                *. *** ***********:**  :  ******    .***:***:.:*** ***  : ::::.

C.perfringens   PDFIQPESRKNEMLNNFLRPGLQDLCVSRTSFTWGIPVSFDEKHVIYVWIDALSNYITAL   238
C.acetobutylicum PDFIQPESRKNEMLNNFLKPGLQDLCISRSSFDWGIPITFDEKHVIYVWIDALSNYITAL   239
C.tetani        PHFIQPESRKNEMLNNFLKPGLQDLCISRTSFDWGIPVSFDNKHVIYVWIDALSNYITAL   238
C.difficile     -SFCFPAARKNEMVANFLDKGLEDLSVTRTTFDWGIKVPFDEKHVIYVWVDALCNYITAL   237
                 *  *  :*****: ***  **:**.::*:* *** :.**:*******:***.******

C.perfringens   GYGQENQELYKKFWPADVHLIGKDILRFHTIYWPIMLMALGLELPKQVFGHGWLLVDGGK   298
C.acetobutylicum GYGSDNDELYNKFWPADLHLVGKDIIRFHTIYWPIMLMALDLPLPKQVFGHGWLLVDGGK   299
C.tetani        GYNSDNQELLEKFWPANVHLVGKDILRFHTIYWPIMLMALGIELPKQVFGHGWLLVDGGK   298
C.difficile     GYMTDNDEEFKKYWPANVQIVGKEIVRFHTIIWPALLMALGLEVPKQVFGHGWILFADDK   297
                **   :*:*   :*:***::::**.*:*****   **    :****.:  :*********:*.  ..*

C.perfringens   MSKSKGNVVDPVVLVNMFGADAVRYYLLREIPFGSDGLFNNEIFIKKVNTDLANDLGNLL   358
C.acetobutylicum MSKSKGNVVDPVVLINEFGTDPVRYYLLHEIPFGSDGLFNNEIFIKKINSDLANDLGNLV   359
C.tetani        MSKSKGNVVDPVVLVDHFGEDTVRYYLLREIPFGSDGLFNNELFIKKINSDLANDLGNLL   358
C.difficile     MSKSKGNVVYPEPIIERYGIDTLKYFLLREFAFGQDGSYTHRNFVTRINYDLANDLGNLI   357
                *********   *    :::  :*  *.::*:**:*:..**.**   :::. *:.::* *********:

C.perfringens   SRTIAMVYKYFGGVIQAPTCKEPIDDELINLALSTPGKVEASIDALKIPEALESIWTLIS   418
C.acetobutylicum SRTAAMIEKYFDGSIQPPVDKEEIDNELIDMAISLPEKLDEDIKKLKIPEALDHIWDLIK   419
C.tetani        SRTVAMVQKYFNGIMPAPIAKEPIDDELINLALDTREKVENNMEKLKIPEVLDEIWTLIG   418
C.difficile     SRTVAMVEKYNNGIIPTAKVSTDFDADLKEQAVSTRENFEAEMDKMQFHEALESVWKLVR   417
                *** **: **  .*  :  ..   .:* :*  *:.    .:   .:.   :::  *.*:  :*  *:

C.perfringens   RANKYIDETTPWILAKDEEKKERLGTVLYNLLETLRFVSVMISPFLTETSVKINAQLNTK   478
C.acetobutylicum RANKYIDETTPWVLAKDENKKARLGTVLYNLVESLRFVATTLTPFLPETGEKIKTQLNIE   479
C.tetani        RANKYIDETTPWILAKDEDKKDRLGTVLYNLSETLRIISVLISAFIPKTSERINEQLNVD   478
C.difficile     RTNKYIDETMPWALAKDETKKGELDTVLYNLCESIRIIATLINPIMNETANKIYEHIGIK   477
                *:*******  **  ***** **  .*.******  *::*::::  .:.:::.::*.   :*   :::..

C.perfringens   ----VTTWESLKEFNGTVAGDKVVKGDVIFPRIDVEEKLAELEALKPAPVKPANEELVEN   534
C.acetobutylicum ----LDTWESLSAFDGTRAGTKVSKGEVIFPRIDVDKKIEELNKLKEEQLKAT---RKMQ   532
C.tetani        ----LTTWDSIASFDGTKAGTKVVKGDALFPRIDVEAKIEELNSLKEKKEKKE-----IK   529
C.difficile     GQDDITTWESTKTFGLIGENVKVFKGEPLFPRLDVEKEIEELTKMFSGKPPVE---EKPL   534
                  :   **:*  *.  .  ** **:  :***:**: :: **  :

C.perfringens   PIKEEITIDDDFDKIDLRVVKVLECEPVKKAKKLLKLKVDLGGEERQVISGIAQYYKPEEL   594
C.acetobutylicum PLKPEISIDDVDKLDLRVVKVLECEPVKKSKKLLKLKVELGGEERQVLSGISQFYKPEDL   592
C.tetani        PIKEEITIDDDFDKIDLRVVKVISCEPVKGAKKLLKLKVDLGGEERQVISGIAQYYKPEEL   589
C.difficile     EHKEEITIDDLDKIELRVGKIISCEKHPKANKLLVSQVKIGPETRQIVSGIAEYYKPEDL   594
                  * **:***.**  :**** *:: .**      ::***    :*..:* * **::***:::****:*

C.perfringens   VGKYVVLVANLKPVKLRGELSQGMILAAAPSDDSELLLVN-PGEMLTGSQVR   645
C.acetobutylicum IGKKVVLVANLKPAKLMGQLSQGMILAVATDDDSKLYTLDIPEDIPTGSIVR   644
```

TABLE 1-continued

Alignment of Clostridium Family Member MetRS amino acid sequence

```
C.tetani     VGKSVVLVANLKPAKLRGELSQGMILAAATDDDSKLFTVSIPGELPTGSQVR      641
C.difficile  VGKEVTVVCNLKPVKLRGVESQGMILAAG--DDGEPYVLPFTQGAKDGCEVR      644
             :** *.:*.****.** * *******.. **.:    :  .    *. **
```

Analysis of SEQ ID NOS: 3, 4, 5 and 6 indicate that the MetRS amino acid sequence is highly conserved within the Clostridium family. This data indicates that inhibitors having potent activity against C. difficile will also have potent activity against other Clostridium family members.

Example 5

Compounds of the Present Invention Show Strong Therapeutic Utility During In Vivo Trials Animal studies were performed to determine the efficacy of MetRS inhibitors for treating C. difficile-infections. The MetRS inhibitors tested were two compounds of formula (II), 5-[3-((R)-6,8-Dibromo-chroman-4-ylamino)-propylamino]-4H-thieno[3,2-b]pyridine-7-one (both racemic mixture and the R enantiomer) and 5-[3-((R)-8-Bromo-6-chloro-chroman-4-ylamino)-propylamino]-4H-thieno[3,2-b]pyridin-7-one. Also tested was a compound of formula (IV), 2-(3-{3,5-Dibromo-2-[2-(4-methyl-thiazol-5-yl)-ethoxy]-benzylamino}-propylamino)-1H-quinolin-4-one.

Results were compared to C. difficile-infected hamsters treated with the conventional antibiotic, vancomycin. Infected hamsters were treated with either a solution or suspension of a MetRS inhibitor at 5 to 50 mg/kg or vancomycin at 2.5, 5 or 25 mg/kg. There were eight hamsters per group with the final endpoint of the experiment being survival. Expired hamsters were examined for GI condition.

Data for the studies indicated that control hamsters (infected with C. difficile but receiving no treatment) died within 3-4 days. Hamsters treated with MetRS inhibitors showed a significant increase in survival, often living until study termination, typically 28 or more days. These results were similar or superior to the results obtained using vancomycin treatment. 5-[3-((R)-6,8-Dibromo-chroman-4-ylamino)-propylamino]-4H-thieno[3,2-b]pyridine-7-one demonstrated the best efficacy. 5-[3-((R)-6,8-Dibromo-chroman-4-ylamino)-propylamino]-4H-thieno[3,2-b]pyridine-7-one exhibited superior efficacy to vancomycin in that >60% survival was observed on Day 28 (5 mg/kg BID) as compared to 0-10% survival with vancomycin. Surviving animals had healthy GI appearance and histopathology. Low systemic exposure and bioavailability was observed in hamsters following oral administration of the MetRS inhibitors.

The data in this Example illustrates that the compounds of the present invention were comparable or superior to vancomycin in their capability to treat animals infected with C. difficile.

Example 6

Compounds of the Present Invention Effect Toxin Production in C. difficile

The pathogenicity of C. difficile is associated with its ability to produce the extracellular toxins A and B. Hypertoxinogenic strains are responsible for recent outbreaks with high mortality. In contrast, isolates that do not produce toxins are non-pathogenic. Since toxin production requires active protein synthesis, inhibition of the protein synthesis machinery is expected to suppress de novo toxin production. Therefore, MetRS inhibitors were evaluated for their effect on C. difficile toxin production in vitro.

Methods:

C. difficile strain ATCC43255 was grown and maintained anaerobically on CDC anaerobe agar (Remel, Lenexa, Kans.). To test the effect of antibacterial agents on growth, cells were grown anaerobically for 40 h at 35° C. in 96-well brain heart infusion (BHI) broth cultures, with an initial inoculum of $10^6$ CFU/mL. To test the effect of antibacterial agents on toxin production at high C. difficile cell densities, the cells were grown anaerobically for 24 h at 35° C. in 96-well brain heart infusion (BHI) broth cultures. Spent medium was then replaced with fresh broth containing MetRS inhibitors and control agents at a concentration range of 0.015-16 µg/mL. After 4 days, growth and cell viability were monitored by optical density measurements at 595 nm and by culture on CDC anaerobe agar, respectively. Culture supernatants were collected, and toxin A was detected by ELIFA (enzyme-linked immuno-flow assay) using an anti toxin A monoclonal antibody (Novus Biologicals, Centennial, Colo.).

Results:

The MetRS inhibitors 5-[3-(6,8-Dibromo-chroman-4-ylamino)-propylamino]-4H-thieno[3,2-b]pyridin-7-one and 5-(3-{3,5-Dibromo-2-[2-(4-methyl-thiazol-5-yl)-ethoxy]-benzylamino}-propylamino)-4H-thieno[3,2-b]pyridin-7-one prevented growth of C. difficile in broth at concentrations of ≥0.25 µg/mL.

Toxin production in high cell density, 4 day old stationary phase cultures was inhibited by four different MetRS inhibitors (5-[3-(6,8-Dibromo-chroman-4-ylamino)-propylamino]-4H-thieno[3,2-b]pyridin-7-one, 5-(3-{3,5-Dibromo-2-[2-(4-methyl-thiazol-5-yl)-ethoxy]-benzylamino}-propylamino)-4H-thieno[3,2-b]pyridin-7-one, R-(+)-5-[3-(6,8-Dibromo-chroman-4-ylamino)-propylamino]-4H-thieno[3,2-b]pyridin-7-one di-hydrochloride, 5-[3-(6,8-Dibromo-1,2,3,4-tetrahydro-quinolin-4-ylamino)-propylamino]-4H-thieno[3,2-b]pyridin-7-one tri-hydrochloride) at concentrations as low as 0.25 µg/mL. In contrast, much higher concentrations (4->16 µg/mL) of the comparator agents (metronidazole, vancomycin, levofloxacin) were required to inhibit toxin production.

Conclusions:

MetRS inhibitors demonstrate inhibitory effects on both growth and toxin production of C. difficile in broth cultures. Furthermore, toxin production was effectively blocked in stationary phase cultures. As a consequence of this suppression of toxin production by bacteriostatic MetRS inhibitors, C. difficile becomes essentially non-toxinogenic and thus non-pathogenic. This effect is unique to protein synthesis inhibitors, such as MetRS inhibitors, whose mode-of-action does not require that the bacteria are actively growing.

Example 7

Compounds of the Present Invention Effect Spore Production in C. Difficile

C. difficile is an organism well known for its ability to form spores that are resistant to heating, drying and many cleaning agents such as disinfectants. Spores present in the environment may serve as a reservoir for disease-causing organisms. *C. difficile* infections are often initiated by the ingestion of spores that germinate in the GI tract causing CDAD. Spore retention in the gut after treatment of CDAD is also thought to be a major source of relapsing disease. Reduction in the capacity of *C. difficile* to produce spores or spore germination could represent an important breakthrough in the treatment of this disease. Spore coats are composed primarily of protein, generation of the spore coat requires protein synthesis and inhibition of active protein synthesis is expected to affect spore production in this organism. Therefore, MetRS inhibitors were evaluated for their effect on *C. difficile* spore production in vitro.

Methods:

MetRS inhibitors were evaluated for their effect on sporulation of four clinical isolates of *C. difficile*, including two recent outbreak isolates that belong to the BI/NAP1 genotype. *C. difficile* strains were grown on supplemented *Brucella* blood for 24 to 48 hours and colonies suspended in saline to achieve a turbidity equivalent to a 0.5 McFarland standard. *C. difficile* suspensions (10 µL) were spread onto the surface of fresh supplemented *Brucella* agar plates with 5% laked sheep blood containing MetRS inhibitors at concentrations ranging from 0.06 to 2 µg/mL and incubated anaerobically at 35° C. for 96 hours. Aliquots of the same cell suspensions used to inoculate the MetRS containing plates were also plated for viable counts and an additional 250 µL aliquot was treated with 250 µL of absolute ethanol for 1 hour at room temperature to eliminate vegetative cells and permit the enumeration of spores. The ratio of spores to total cells was again determined for all four strains after 96 hours of incubation in the presence of compound and used to compare the effects of MetRS inhibitors with drug free controls on sporulation rates.

Results:

Three out of four *C. difficile* strains produced measurable number of spores and were evaluated as described above. Treatment of all strains with 5-[3-((R)-6,8-Dibromo-chroman-4-ylamino)-propylamino]-4H-thieno[3,2-b]pyridine-7-one in all strains showed reductions in spore production at 0.25×MIC (<2% spores) and at 0.5×MIC (<1% spores). This is in marked contrast to the results obtained after treatment with metronidazole, where all tested strains display marked increases in spore production (up to 100% spores) after exposure to subMIC concentrations of the drug. Treatment with vancomycin induced similar spore production increases in two strains but not in one strain where the spore counts remained low.

Conclusions:

5-[3-((R)-6,8-Dibromo-chroman-4-ylamino)-propylamino]-4H-thieno[3,2-b]pyridine-7-one at subMIC (0.25 and 0.5×MIC) was effective in preventing vegetative cells of *C. difficile* from forming spores. These data suggest that 5-[3-((R)-6,8-Dibromo-chroman-4-ylamino)-propylamino]-4H-thieno[3,2-b]pyridine-7-one might also have a useful role in preventing outbreaks and reducing relapse rates that have been correlated with widespread prevalence of *C. difficile* spores in the environment.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

The invention claimed is:

1. A method of treating a *Clostridium difficile* based infection in a mammal comprising administering to the mammal an effective amount of a MetRS inhibitor compound represented by a compound of formula (IIa):

(IIa)

in which:
X is selected from the group consisting of NH, O, S, SO, SO$_2$, or CH$_2$;
n is 1, 2 or 3;
* indicates an asymmetric carbon atom, wherein when n is 2 or 3, then * is R configuration; wherein when n is 1 and X is CH$_2$, then * is R configuration; and wherein when n is 1 and X is selected from the group consisting of NH, O, S, SO, or SO$_2$, then * is S configuration;
m is 0, 1, 2, 3, or 4;
R$^1$ is independently selected from halo, cyano, hydroxyl, (C$_{1-6}$)alkyl (optionally substituted by halo, hydroxyl, amino, carboxy, or (C$_{1-6}$)alkoxycarbonyl), (C$_{3-7}$)cycloalkyl, C$_{(1-6)}$alkoxy, amino, mono- or di-(C$_{1-6}$)alkylamino, acylamino, carboxy, (C$_{1-6}$)alkoxycarbonyl, carboxy(C$_{1-6}$)alkyloxy, (C$_{1-6}$)alkylthio, (C$_{1-6}$)alkylsulphinyl, (C$_{1-6}$)alkylsulphonyl, sulphamoyl, mono- and di-(C$_{1-6}$)alkylsulphamoyl, carbamoyl, mono- and di-(C$_{1-6}$)alkylcarbamoyl and heterocyclic;
R$^2$ is independently selected from halo, cyano, hydroxyl, (C$_{1-6}$)alkyl (optionally substituted by halo, hydroxyl, amino, carboxy, or (C$_{1-6}$)alkoxycarbonyl), (C$_{3-7}$)cycloalkyl, C$_{(1-6)}$alkoxy, amino, mono- or di-(C$_{1-6}$)alkylamino, acylamino, carboxy, (C$_{1-6}$)alkoxycarbonyl, carboxy(C$_{1-6}$)alkyloxy, (C$_{1-6}$)alkylthio, (C$_{1-6}$)alkylsulphinyl, (C$_{1-6}$)alkylsulphonyl, sulphamoyl, mono- and di-(C$_{1-6}$)alkylsulphamoyl, carbamoyl, mono- and di-(C$_{1-6}$)alkylcarbamoyl and heterocyclic; and
when Z$_1$ is S, Z$_2$ and Z$_3$ are CH; when Z$_2$ is S, Z$_1$ and Z$_3$ are CH; and when Z$_3$ is S, Z$_1$ and Z$_2$ are CH.

2. The method of claim 1 wherein the MetRS inhibitor is selected from the group consisting of:
5-[3-((R)(−)-5,7-Dibromo-1,2,3,4-tetrahydro-naphthalen-1-ylamino)-propylamino]-4H-thieno[3,2-b]pyridine-7-one;
5-[3-((R)(+)-8-Bromo-6-chloro-chroman-4-ylamino)-propylamino]-4H-thieno[3,2-b]pyridine-7-one;
5-[3-((R)(+)-6,8-Dibromo-1,2,3,4-tetrahydro-quinolin-4-ylamino)-propylamino]-4H-thieno[3,2-b]pyridine-7-one;
5-[3-((R)(+)-6,8-Dibromo-chroman-4-ylamino)-propylamino]-4H-thieno[3,2-b]pyridine-7-one;
and
5-[3-((S)-5,7-Dibromo-2,3-dihydro-benzofuran-3ylamino)-propylamino]-4H-thieno[3,2-b]pyridine-7-one.

* * * * *

SEQUENCE LISTING

```
<160> NUMBER OF SEQ ID NOS: 6

<210> SEQ ID NO 1
<211> LENGTH: 33
<212> TYPE: DNA
<213> ORGANISM: Artificial
<220> FEATURE:
<223> OTHER INFORMATION: Primer

<400> SEQUENCE: 1
ctgcagagct agcaaaccga gttttatgt aac                              33

<210> SEQ ID NO 2
<211> LENGTH: 33
<212> TYPE: DNA
<213> ORGANISM: Artificial
<220> FEATURE:
<223> OTHER INFORMATION: Primer

<400> SEQUENCE: 2
ctttctaagc ttctactaac gaacctcgga tcc                             33

<210> SEQ ID NO 3
<211> LENGTH: 645
<212> TYPE: PRT
<213> ORGANISM: Clostridium perfringens

<400> SEQUENCE: 3

Met Cys Lys Lys Pro Tyr Tyr Ile Thr Thr Pro Ile Tyr Tyr Pro Ser
1               5                   10                  15
```

-continued

Thr Asn Leu His Ile Gly Asn Thr Tyr Thr Thr Val Ala Ala Asp Ala
            20                  25                  30

Ile Ala Arg Phe Lys Arg Leu Thr Gly His Glu Val Met Phe Leu Thr
            35                  40                  45

Gly Thr Asp Glu His Gly Gln Lys Ile Glu Arg Ile Ala Asn Glu Lys
50                  55                  60

Gly Ile Thr Pro Lys Glu His Val Asp Glu Ile Val Ala Gly Ile Lys
65                  70                  75                  80

Asp Leu Trp Lys Met Met Asn Ile Ser Tyr Asp Lys Phe Ile Arg Thr
                85                  90                  95

Thr Asp Asp Tyr His Val Lys Ala Val Gln Glu Ile Phe Lys Lys Leu
            100                 105                 110

Tyr Asp Gln Gly Asp Ile Tyr Lys Asp Ser Tyr Glu Gly Leu Tyr Cys
            115                 120                 125

Thr Pro Cys Glu Ser Phe Trp Thr Glu Thr Gln Leu Val Asn Gly Asn
            130                 135                 140

Cys Pro Asp Cys Gly Arg Pro Val Glu Lys Ala Lys Glu Glu Ala Tyr
145                 150                 155                 160

Phe Phe Lys Met Ser Lys Tyr Ala Asp Arg Leu Ile Gln Tyr Ile Glu
                165                 170                 175

Glu His Pro Asp Phe Ile Gln Pro Glu Ser Arg Lys Asn Glu Met Leu
            180                 185                 190

Asn Asn Phe Leu Arg Pro Gly Leu Gln Asp Leu Cys Val Ser Arg Thr
            195                 200                 205

Ser Phe Thr Trp Gly Ile Pro Val Ser Phe Asp Glu Lys His Val Ile
210                 215                 220

Tyr Val Trp Ile Asp Ala Leu Ser Asn Tyr Ile Thr Ala Leu Gly Tyr
225                 230                 235                 240

Gly Gln Glu Asn Gln Glu Leu Tyr Lys Lys Phe Trp Pro Ala Asp Val
                245                 250                 255

His Leu Ile Gly Lys Asp Ile Leu Arg Phe His Thr Ile Tyr Trp Pro
            260                 265                 270

Ile Met Leu Met Ala Leu Gly Leu Glu Leu Pro Lys Gln Val Phe Gly
            275                 280                 285

His Gly Trp Leu Leu Val Asp Gly Gly Lys Met Ser Lys Ser Lys Gly
            290                 295                 300

Asn Val Val Asp Pro Val Val Leu Val Asn Met Phe Gly Ala Asp Ala
305                 310                 315                 320

Val Arg Tyr Tyr Leu Leu Arg Glu Ile Pro Phe Gly Ser Asp Gly Leu
                325                 330                 335

Phe Asn Asn Glu Ile Phe Ile Lys Lys Val Asn Thr Asp Leu Ala Asn
            340                 345                 350

Asp Leu Gly Asn Leu Leu Ser Arg Thr Ile Ala Met Val Tyr Lys Tyr
            355                 360                 365

Phe Gly Gly Val Ile Gln Ala Pro Thr Cys Lys Glu Pro Ile Asp Asp
            370                 375                 380

Glu Leu Ile Asn Leu Ala Leu Ser Thr Pro Gly Lys Val Glu Ala Ser
385                 390                 395                 400

Ile Asp Ala Leu Lys Ile Pro Glu Ala Leu Glu Ser Ile Trp Thr Leu
                405                 410                 415

Ile Ser Arg Ala Asn Lys Tyr Ile Asp Glu Thr Thr Pro Trp Ile Leu
            420                 425                 430

Ala Lys Asp Glu Glu Lys Lys Glu Arg Leu Gly Thr Val Leu Tyr Asn

```
                    435                 440                 445
Leu Leu Glu Thr Leu Arg Phe Val Ser Val Met Ile Ser Pro Phe Leu
            450                 455                 460
Thr Glu Thr Ser Val Lys Ile Asn Ala Gln Leu Asn Thr Lys Val Thr
465                 470                 475                 480
Thr Trp Glu Ser Leu Lys Glu Phe Asn Gly Thr Val Ala Gly Asp Lys
                485                 490                 495
Val Val Lys Gly Asp Val Ile Phe Pro Arg Ile Asp Val Glu Lys
            500                 505                 510
Leu Ala Glu Leu Glu Ala Leu Lys Pro Ala Pro Val Lys Pro Ala Asn
            515                 520                 525
Glu Glu Leu Val Glu Asn Pro Ile Lys Glu Ile Thr Ile Asp Asp
            530                 535                 540
Phe Asp Lys Ile Asp Leu Arg Val Val Lys Val Leu Glu Cys Glu Pro
545                 550                 555                 560
Val Lys Lys Ala Lys Lys Leu Leu Lys Leu Lys Val Asp Leu Gly Gly
                565                 570                 575
Glu Glu Arg Gln Val Ile Ser Gly Ile Ala Gln Tyr Tyr Lys Pro Glu
            580                 585                 590
Glu Leu Val Gly Lys Tyr Val Val Leu Val Ala Asn Leu Lys Pro Val
            595                 600                 605
Lys Leu Arg Gly Glu Leu Ser Gln Gly Met Ile Leu Ala Ala Ala Pro
            610                 615                 620
Ser Asp Asp Ser Glu Leu Leu Leu Val Asn Pro Gly Glu Met Leu Thr
625                 630                 635                 640
Gly Ser Gln Val Arg
                645

<210> SEQ ID NO 4
<211> LENGTH: 644
<212> TYPE: PRT
<213> ORGANISM: Clostridium acetobutylicum

<400> SEQUENCE: 4

Met Ser Glu Lys Lys Phe Tyr Ile Thr Thr Pro Ile Tyr Tyr Pro
1               5                   10                  15
Ser Ala Lys Leu His Ile Gly Asn Thr Tyr Thr Thr Val Ala Ser Asp
                20                  25                  30
Ala Leu Val Arg Phe Lys Arg Leu Gln Gly Tyr Asp Ala Phe Met Leu
            35                  40                  45
Thr Gly Thr Asp Glu His Gly Gln Lys Ile Gln Arg Ile Ala Glu Asp
    50                  55                  60
Lys Gly Ile Thr Pro Lys Ala Tyr Val Asp Glu Ile Val Ala Gly Ile
65                  70                  75                  80
Lys Asp Leu Trp Lys Met Met Asn Ile Ser Tyr Asp Lys Phe Ile Arg
                85                  90                  95
Thr Thr Asp Glu Glu His Val Lys Ala Val Gln Lys Ile Val Lys Lys
            100                 105                 110
Phe Tyr Asp Asn Gly Asp Ile Tyr Lys Ser Ala Tyr Glu Gly Trp Tyr
        115                 120                 125
Cys Thr Pro Cys Glu Ser Phe Trp Thr Glu Thr Gln Leu Val Asp Gly
    130                 135                 140
Lys Cys Pro Asp Cys Gly Arg Pro Val Glu Lys Thr Lys Glu Glu Ala
145                 150                 155                 160

Tyr Phe Phe Lys Met Ser Lys Tyr Ala Asp Arg Leu Ile Lys Tyr Ile
```

```
                    165                 170                 175
Glu Asp His Pro Asp Phe Ile Gln Pro Glu Ser Arg Lys Asn Glu Met
            180                 185                 190
Leu Asn Asn Phe Leu Lys Pro Gly Leu Gln Asp Leu Cys Ile Ser Arg
            195                 200                 205
Ser Ser Phe Asp Trp Gly Ile Pro Ile Thr Phe Asp Glu Lys His Val
            210                 215                 220
Ile Tyr Val Trp Ile Asp Ala Leu Ser Asn Tyr Ile Thr Ala Leu Gly
225                 230                 235                 240
Tyr Gly Ser Asp Asn Asp Glu Leu Tyr Asn Lys Phe Trp Pro Ala Asp
                245                 250                 255
Leu His Leu Val Gly Lys Asp Ile Ile Arg Phe His Thr Ile Tyr Trp
            260                 265                 270
Pro Ile Met Leu Met Ala Leu Asp Leu Pro Leu Pro Lys Gln Val Phe
            275                 280                 285
Gly His Gly Trp Leu Leu Val Asp Gly Gly Lys Met Ser Lys Ser Lys
            290                 295                 300
Gly Asn Val Val Asp Pro Val Val Leu Ile Asn Glu Phe Gly Thr Asp
305                 310                 315                 320
Pro Val Arg Tyr Tyr Leu Leu His Glu Ile Pro Phe Gly Ser Asp Gly
                325                 330                 335
Leu Phe Asn Asn Glu Ile Phe Ile Lys Lys Ile Asn Ser Asp Leu Ala
            340                 345                 350
Asn Asp Leu Gly Asn Leu Val Ser Arg Thr Ala Ala Met Ile Glu Lys
            355                 360                 365
Tyr Phe Asp Gly Ser Ile Gln Pro Val Asp Lys Glu Glu Ile Asp
            370                 375                 380
Asn Glu Leu Ile Asp Met Ala Ile Ser Leu Pro Gly Lys Leu Asp Glu
385                 390                 395                 400
Asp Ile Lys Lys Leu Lys Ile Pro Glu Ala Leu Asp His Ile Trp Asp
                405                 410                 415
Leu Ile Lys Arg Ala Asn Lys Tyr Ile Asp Glu Thr Thr Pro Trp Val
            420                 425                 430
Leu Ala Lys Asp Glu Asn Lys Lys Ala Arg Leu Gly Thr Val Leu Tyr
            435                 440                 445
Asn Leu Val Glu Ser Leu Arg Phe Val Ala Thr Thr Leu Thr Pro Phe
            450                 455                 460
Leu Pro Glu Thr Gly Glu Lys Ile Lys Thr Gln Leu Asn Ile Glu Leu
465                 470                 475                 480
Asp Thr Trp Glu Ser Leu Ser Ala Phe Asp Gly Thr Arg Ala Gly Thr
                485                 490                 495
Lys Val Ser Lys Gly Glu Val Ile Phe Pro Arg Ile Asp Val Asp Lys
            500                 505                 510
Lys Ile Glu Glu Leu Asn Lys Leu Lys Glu Gln Leu Lys Ala Thr
            515                 520                 525
Arg Lys Met Gln Pro Leu Lys Pro Glu Ile Ser Ile Asp Asp Val Asp
            530                 535                 540
Lys Leu Asp Leu Arg Val Val Lys Val Leu Glu Cys Glu Pro Val Lys
545                 550                 555                 560
Lys Ser Lys Lys Leu Leu Lys Leu Val Glu Leu Gly Gly Glu
                565                 570                 575
Arg Gln Val Leu Ser Gly Ile Ser Gln Phe Tyr Lys Pro Glu Asp Leu
            580                 585                 590
```

```
Ile Gly Lys Lys Val Val Leu Val Ala Asn Leu Lys Pro Ala Lys Leu
        595                 600                 605

Met Gly Gln Leu Ser Gln Gly Met Ile Leu Ala Val Ala Thr Asp Asp
        610                 615                 620

Asp Ser Lys Leu Tyr Thr Leu Asp Ile Pro Glu Asp Ile Pro Thr Gly
625                 630                 635                 640

Ser Ile Val Arg

<210> SEQ ID NO 5
<211> LENGTH: 641
<212> TYPE: PRT
<213> ORGANISM: Clostridium tetani

<400> SEQUENCE: 5

Met Asn Lys Lys Thr Phe Tyr Ile Thr Thr Pro Ile Tyr Tyr Pro Ser
1               5                   10                  15

Ala Lys Leu His Ile Gly Asn Thr Tyr Thr Thr Val Ala Ala Asp Ala
            20                  25                  30

Leu Ala Arg Phe Lys Arg Leu Thr Gly His Asp Val Leu Phe Leu Thr
        35                  40                  45

Gly Thr Asp Glu His Gly Gln Lys Ile Gln Arg Val Ala Glu Glu Lys
    50                  55                  60

Gly Leu Lys Pro Lys Glu Tyr Leu Asp Asn Met Val Asp Ser Ile Lys
65                  70                  75                  80

Glu Leu Trp Lys Ser Met Asn Ile Ser Tyr Asp Lys Phe Ile Arg Thr
                85                  90                  95

Thr Asp Asp Tyr His Ile Glu Ser Val Gln Lys Ile Phe Lys Lys Leu
            100                 105                 110

Tyr Glu Gln Gly Asp Ile Tyr Lys Gly Glu Tyr Glu Gly Trp Tyr Cys
        115                 120                 125

Thr Pro Cys Glu Ser Phe Trp Thr Glu Ser Gln Leu Asp Asp His Asn
    130                 135                 140

Cys Pro Asp Cys Gly Arg Pro Val Glu Lys Thr Lys Glu Glu Ala Tyr
145                 150                 155                 160

Phe Phe Lys Met Ser Lys Tyr Ala Asp Arg Leu Ile Lys Tyr Ile Glu
                165                 170                 175

Glu Asn Pro His Phe Ile Gln Pro Glu Ser Arg Lys Asn Glu Met Leu
            180                 185                 190

Asn Asn Phe Leu Lys Pro Gly Leu Gln Asp Leu Cys Ile Ser Arg Thr
        195                 200                 205

Ser Phe Asp Trp Gly Ile Pro Val Ser Phe Asp Asn Lys His Val Ile
    210                 215                 220

Tyr Val Trp Ile Asp Ala Leu Ser Asn Tyr Ile Thr Ala Leu Gly Tyr
225                 230                 235                 240

Asn Ser Asp Asn Gln Glu Leu Leu Glu Lys Phe Trp Pro Ala Asn Val
                245                 250                 255

His Leu Val Gly Lys Asp Ile Leu Arg Phe His Thr Ile Tyr Trp Pro
            260                 265                 270

Ile Met Leu Met Ala Leu Gly Ile Glu Leu Pro Lys Gln Val Phe Gly
        275                 280                 285

His Gly Trp Leu Leu Val Asp Gly Gly Lys Met Ser Lys Ser Lys Gly
    290                 295                 300

Asn Val Val Asp Pro Val Val Leu Val Asp His Phe Gly Glu Asp Thr
305                 310                 315                 320

Val Arg Tyr Tyr Leu Leu Arg Glu Ile Pro Phe Gly Ser Asp Gly Leu
```

```
                325                 330                 335
Phe Asn Asn Glu Leu Phe Ile Lys Lys Ile Asn Ser Asp Leu Ala Asn
                340                 345                 350

Asp Leu Gly Asn Leu Leu Ser Arg Thr Val Ala Met Val Gln Lys Tyr
            355                 360                 365

Phe Asn Gly Ile Met Pro Ala Pro Ile Ala Lys Glu Pro Ile Asp Asp
        370                 375                 380

Glu Leu Ile Asn Leu Ala Leu Asp Thr Arg Lys Val Glu Asn Asn
385                 390                 395                 400

Met Glu Lys Leu Lys Ile Pro Glu Val Leu Asp Glu Ile Trp Thr Leu
                405                 410                 415

Ile Gly Arg Ala Asn Lys Tyr Ile Asp Glu Thr Thr Pro Trp Ile Leu
            420                 425                 430

Ala Lys Asp Glu Asp Lys Lys Asp Arg Leu Gly Thr Val Leu Tyr Asn
        435                 440                 445

Leu Ser Glu Thr Leu Arg Ile Ile Ser Val Leu Ile Ser Ala Phe Ile
    450                 455                 460

Pro Lys Thr Ser Glu Arg Ile Asn Glu Gln Leu Asn Val Asp Leu Thr
465                 470                 475                 480

Thr Trp Asp Ser Ile Ala Ser Phe Asp Gly Thr Lys Ala Gly Thr Lys
                485                 490                 495

Val Val Lys Gly Asp Ala Leu Phe Pro Arg Ile Asp Val Glu Ala Lys
            500                 505                 510

Ile Glu Glu Leu Asn Ser Leu Lys Glu Lys Glu Lys Lys Glu Ile
        515                 520                 525

Lys Pro Ile Lys Glu Glu Ile Thr Ile Asp Asp Phe Asp Lys Ile Asp
    530                 535                 540

Leu Arg Val Val Lys Val Ile Ser Cys Glu Pro Val Lys Gly Ala Lys
545                 550                 555                 560

Lys Leu Leu Lys Leu Lys Val Asp Leu Gly Gly Glu Glu Arg Gln Val
                565                 570                 575

Ile Ser Gly Ile Ala Gln Tyr Tyr Lys Pro Glu Glu Leu Val Gly Lys
            580                 585                 590

Ser Val Val Leu Val Ala Asn Leu Lys Pro Ala Lys Leu Arg Gly Glu
        595                 600                 605

Leu Ser Gln Gly Met Ile Leu Ala Ala Ala Thr Asp Asp Ser Lys
    610                 615                 620

Leu Phe Thr Val Ser Ile Pro Gly Glu Leu Pro Thr Gly Ser Gln Val
625                 630                 635                 640

Arg

<210> SEQ ID NO 6
<211> LENGTH: 644
<212> TYPE: PRT
<213> ORGANISM: Clostridium difficile

<400> SEQUENCE: 6

Met Ser Lys Pro Ser Phe Tyr Val Thr Thr Pro Ile Tyr Tyr Pro Ser
1               5                   10                  15

Gly Gly Leu His Ile Gly His Thr Tyr Ser Thr Val Ala Ala Asp Thr
            20                  25                  30

Ile Ala Arg Phe Lys Arg Phe Cys Gly Tyr Asp Val Lys Phe Leu Thr
        35                  40                  45

Gly Thr Asp Glu His Gly Glu Lys Ile Gln Lys Lys Ala Ile Glu Gln
    50                  55                  60
```

-continued

```
Gly Met Ser Glu Ile Glu Tyr Leu Asp Gly Met Ile Lys Asp Ile Lys
65                  70                  75                  80

Ala Leu Trp Asn Thr Met Asp Ile Ser Tyr Asp Asp Phe Ile Arg Thr
                85                  90                  95

Thr Glu Arg His Thr Asp Ile Ile Gln Lys Ile Phe Thr Lys Leu Tyr
            100                 105                 110

Glu Gln Gly Asp Ile Tyr Lys Gly Glu Tyr Glu Gly Arg Tyr Cys Thr
        115                 120                 125

Pro Cys Glu Ser Phe Trp Thr Glu Ser Gln Leu Leu Glu Gly Asn Lys
    130                 135                 140

Cys Pro Asp Cys Gly Arg Glu Thr Tyr Leu Val Lys Glu Glu Ser Tyr
145                 150                 155                 160

Phe Phe Arg Leu Ser Lys Tyr Glu Asp Arg Leu Lys Glu Leu Phe Lys
                165                 170                 175

Asp Asp Ser Phe Cys Phe Pro Ala Ala Arg Lys Asn Glu Met Val Ala
            180                 185                 190

Asn Phe Leu Asp Lys Gly Leu Glu Asp Leu Ser Val Thr Arg Thr Thr
        195                 200                 205

Phe Asp Trp Gly Ile Lys Val Pro Phe Asp Glu Lys His Val Ile Tyr
    210                 215                 220

Val Trp Val Asp Ala Leu Cys Asn Tyr Ile Thr Ala Leu Gly Tyr Met
225                 230                 235                 240

Thr Asp Asn Asp Glu Glu Phe Lys Lys Tyr Trp Pro Ala Asn Val Gln
                245                 250                 255

Ile Val Gly Lys Glu Ile Val Arg Phe His Thr Ile Ile Trp Pro Ala
            260                 265                 270

Leu Leu Met Ala Leu Gly Leu Glu Val Pro Lys Gln Val Phe Gly His
        275                 280                 285

Gly Trp Ile Leu Phe Ala Asp Asp Lys Met Ser Lys Ser Lys Gly Asn
    290                 295                 300

Val Val Tyr Pro Glu Pro Ile Ile Glu Arg Tyr Gly Ile Asp Thr Leu
305                 310                 315                 320

Lys Tyr Phe Leu Leu Arg Glu Phe Ala Phe Gly Gln Asp Gly Ser Tyr
                325                 330                 335

Thr His Arg Asn Phe Val Thr Arg Ile Asn Tyr Asp Leu Ala Asn Asp
            340                 345                 350

Leu Gly Asn Leu Ile Ser Arg Thr Val Ala Met Val Glu Lys Tyr Asn
        355                 360                 365

Asn Gly Ile Ile Pro Thr Ala Lys Val Ser Thr Asp Phe Asp Ala Asp
    370                 375                 380

Leu Lys Glu Gln Ala Val Ser Thr Arg Glu Asn Phe Glu Ala Glu Met
385                 390                 395                 400

Asp Lys Met Gln Phe His Glu Ala Leu Glu Ser Val Trp Lys Leu Val
                405                 410                 415

Arg Arg Thr Asn Lys Tyr Ile Asp Glu Thr Met Pro Trp Ala Leu Ala
            420                 425                 430

Lys Asp Glu Thr Lys Lys Gly Glu Leu Asp Thr Val Leu Tyr Asn Leu
        435                 440                 445

Cys Glu Ser Ile Arg Ile Ala Thr Leu Ile Asn Pro Ile Met Asn
    450                 455                 460

Glu Thr Ala Asn Lys Ile Tyr Glu His Ile Gly Ile Lys Gly Gln Asp
465                 470                 475                 480

Asp Ile Thr Thr Trp Glu Ser Thr Lys Thr Phe Gly Leu Ile Gly Glu
```

```
                         485                 490                 495
Asn Val Lys Val Phe Lys Gly Glu Pro Leu Phe Pro Arg Leu Asp Val
            500                 505                 510

Glu Lys Glu Ile Glu Glu Leu Thr Lys Met Phe Ser Gly Lys Pro Pro
        515                 520                 525

Val Glu Glu Lys Pro Leu Glu His Lys Glu Glu Ile Thr Ile Asp Asp
    530                 535                 540

Leu Asp Lys Ile Glu Leu Arg Val Gly Lys Ile Ile Ser Cys Glu Lys
545                 550                 555                 560

His Pro Lys Ala Asn Lys Leu Leu Val Ser Gln Val Lys Ile Gly Pro
                565                 570                 575

Glu Thr Arg Gln Ile Val Ser Gly Ile Ala Glu Tyr Tyr Lys Pro Glu
                580                 585                 590

Asp Leu Val Gly Lys Glu Val Thr Val Val Cys Asn Leu Lys Pro Val
            595                 600                 605

Lys Leu Arg Gly Val Glu Ser Gln Gly Met Ile Leu Ala Ala Gly Asp
            610                 615                 620

Asp Gly Glu Pro Tyr Val Leu Pro Phe Thr Gln Gly Ala Lys Asp Gly
625                 630                 635                 640

Cys Glu Val Arg
```